United States Patent
Gabrilovich

(10) Patent No.: US 12,295,990 B2
(45) Date of Patent: May 13, 2025

(54) USE OF LACTOFERRIN FOR GENERATING MYELOID-DERIVED SUPPRESSOR CELLS

(71) Applicant: The Wistar Institute of Anatomy and Biology, Philadelphia, PA (US)

(72) Inventor: Dmitry I. Gabrilovich, Villanova, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 812 days.

(21) Appl. No.: 17/291,808

(22) PCT Filed: Aug. 13, 2019

(86) PCT No.: PCT/US2019/046385
§ 371 (c)(1),
(2) Date: May 6, 2021

(87) PCT Pub. No.: WO2020/096672
PCT Pub. Date: May 14, 2020

(65) Prior Publication Data
US 2022/0010273 A1    Jan. 13, 2022

Related U.S. Application Data

(60) Provisional application No. 62/758,125, filed on Nov. 9, 2018, provisional application No. 62/758,128, filed on Nov. 9, 2018.

(51) Int. Cl.
| | | |
|---|---|---|
| A61P 37/06 | (2006.01) | |
| A61K 38/40 | (2006.01) | |
| A61K 39/00 | (2006.01) | |
| C12N 5/078 | (2010.01) | |

(52) U.S. Cl.
CPC ............ *A61K 38/40* (2013.01); *A61K 39/461* (2023.05); *A61K 39/4621* (2023.05); *A61K 39/46433* (2023.05); *A61P 37/06* (2018.01); *C12N 5/0634* (2013.01); *A61K 2239/31* (2023.05); *A61K 2239/38* (2023.05); *C12N 2501/2306* (2013.01); *C12N 2501/73* (2013.01); *C12N 2506/11* (2013.01)

(58) Field of Classification Search
None
See application file for complete search history.

(56) References Cited

U.S. PATENT DOCUMENTS

| | | | |
|---|---|---|---|
| 6,066,469 A | 5/2000 | Kruzel et al. | |
| 6,111,081 A | 8/2000 | Conneely et al. | |
| 6,455,687 B1 | 9/2002 | Kruzel et al. | |
| 6,569,831 B1 | 5/2003 | Legrand et al. | |
| 7,183,381 B2 | 2/2007 | Varadhachary et al. | |
| 7,253,143 B1 | 8/2007 | Hanson et al. | |
| 7,354,902 B2 | 4/2008 | Legrand et al. | |
| 7,420,033 B2 | 9/2008 | Varadhachary et al. | |
| 8,673,839 B2 | 3/2014 | Nojima et al. | |
| 8,815,812 B2 | 8/2014 | Mattsby-Baltzer et al. | |
| 2007/0142292 A1 | 6/2007 | Varadhachary et al. | |
| 2011/0009313 A1 | 1/2011 | Sato | |
| 2011/0053833 A1 | 3/2011 | Mattsby-Baltzer et al. | |
| 2012/0184483 A1 | 7/2012 | Faure et al. | |
| 2014/0357550 A1 | 12/2014 | Shmarov et al. | |
| 2018/0127486 A1 | 5/2018 | Kruzel et al. | |

FOREIGN PATENT DOCUMENTS

| | | |
|---|---|---|
| CN | 105664174 | 6/2019 |
| EP | 2030980 | 3/2009 |
| EP | 2668205 | 12/2013 |
| JP | 5427170 | 2/2014 |
| WO | WO 2002/064750 | 8/2002 |
| WO | WO 2008/003688 | 1/2008 |
| WO | WO 2014/099134 | 6/2014 |
| WO | WO 2017/044979 | 3/2017 |
| WO | WO 2017/048822 | 3/2017 |

OTHER PUBLICATIONS

Liu et al., J Clin Invest. Oct. 1, 2019;129(10):4261-4275 (Year: 2019).*
Ammendolia et al., Bovine lactoferrin-derived peptides as novel broad-spectrum inhibitors of influenza virus. Pathog Glob Health. Mar. 2012;106(1):12-9.
Barboza et al., Glycosylation of human milk lactoferrin exhibits dynamic changes during early lactation enhancing its role in pathogenic bacteria-host interactions. Mol Cell Proteomics. Jun. 2012;11(6):M111.015248. Epub Jan. 19, 2012.
Bronte et al., Recommendations for myeloid-derived suppressor cell nomenclature and characterization standards. Nat Commun. Jul. 6, 2016;7:12150.
Fan et al., Interrogating Parkinson's disease LRRK2 kinase pathway activity by assessing Rab 10 phosphorylation in human neutrophils. Biochem J. Jan. 2, 2018;475(1):23-44.
Hammerich, L., & Tacke, F., Emerging roles of myeloid derived suppressor cells in hepatic inflammation and fibrosis. World J Gastrointest Pathophysiol. Aug. 15, 2015;6(3):43-50.
Hayes et al., Phase IB trial of oral talactoferrin in the treatment of patients with metastatic solid tumors. Invest New Drugs. Apr. 2010;28(2):156-62. Epub Feb. 24, 2009.
He et al., Transitory presence of myeloid-derived suppressor cells in neonates is critical for control of inflammation. Nat Med. Feb. 2018;24(2):224-231. Epub Jan. 15, 2018.
Heideveld et al., CD14+ cells from peripheral blood positively regulate hematopoietic stem and progenitor cell survival resulting in increased erythroid yield. Haematologica. Nov. 2015;100(11):1396-406. Epub Aug. 20, 2015.
Hofman et al., Increased Escherichia coli phagocytosis in neutrophils that have transmigrated across a cultured intestinal epithelium. Infect Immun. Feb. 2000;68(2):449-55.

(Continued)

*Primary Examiner* — Daniel C Gamett
(74) *Attorney, Agent, or Firm* — Howson & Howson, LLP; Colleen M. Schaller; Richard F. Kane

(57) ABSTRACT

Provided herein are methods of generating MDSCs ex vivo. The methods include culturing blood cells with lactoferrin.

17 Claims, 24 Drawing Sheets

Specification includes a Sequence Listing.

(56) References Cited

OTHER PUBLICATIONS

Jie et al., Large-scale ex vivo generation of human neutrophils from cord blood CD34+ cells. PLoS One. Jul. 11, 2017;12(7):e0180832.
King et al., A double-blind, placebo-controlled, pilot study of bovine lactoferrin supplementation in bottle-fed infants. J Pediatr Gastroenterol Nutr. Feb. 2007;44(2):245-51.
Kuhns et al., Isolation and Functional Analysis of Human Neutrophils. Curr Protoc Immunol. Nov. 2, 2015;111:7.23.1-7.23.16.
Li et al., A critical concentration of neutrophils is required for effective bacterial killing in suspension. Proc Natl Acad Sci U S A. Jun. 11, 2002;99(12):8289-94.
Liu et al., Lactoferrin-induced myeloid-derived suppressor cell therapy attenuates pathologic inflammatory conditions in newborn mice. J Clin Invest. Oct. 1, 2019;129(10):4261-4275.
Lyons et al., The hidden structure of overimitation. Proc Natl Acad Sci U S A. Dec. 11, 2007;104(50):19751-6. Epub Dec. 4, 2007.
Mandle et al., Infection of human CD34+ progenitor cells with Bartonella henselae results in intraerythrocytic presence of B. henselae. Blood. Aug. 15, 2005;106(4):1215-22. Epub Apr. 28, 2005.
Montagne et al., Changes in lactoferrin and lysozyme levels in human milk during the first twelve weeks of lactation. Adv Exp Med Biol. 2001;501:241-7.
Montagne et al., Immunological and nutritional composition of human milk in relation to prematurity and mother's parity during the first 2 weeks of lactation. J Pediatr Gastroenterol Nutr. Jul. 1999;29(1):75-80.
Mueller et al., Efficacy and tolerability of oral lactoferrin supplementation in mild to moderate acne vulgaris: an exploratory study. Curr Med Res Opin. Apr. 2011;27(4):793-7. Epub Feb. 8, 2011.
Ochoa et al., Impact of lactoferrin supplementation on growth and prevalence of Giardia colonization in children. Clin Infect Dis. Jun. 15, 2008;46(12):1881-3.
Ochoa, T., & Cleary, T., Effect of lactoferrin on enteric pathogens. Biochimie. Jan. 2009;91(1):30-4. Epub Apr. 18, 2008.
Oh et al., Neutrophil isolation protocol. J Vis Exp. Jul. 23, 2008;(17):745.
Parikh et al., Randomized, double-blind, placebo-controlled phase II study of single-agent oral talactoferrin in patients with locally advanced or metastatic non-small-cell lung cancer that progressed after chemotherapy. J Clin Oncol. Nov. 1, 2011;29(31):4129-36. Epub Oct. 3, 2011.
Repnik et al., Simple and cost-effective isolation of monocytes from buffy coats. J Immunol Methods. Jul. 2003;278(1-2):283-92.
Sendo et al., Myeloid-derived suppressor cells in non-neoplastic inflamed organs. Inflamm Regen. Sep. 17, 2018;38:19.
Shi et al., Myeloid-derived suppressor cell function is diminished in aspirin-triggered allergic airway hyperresponsiveness in mice. J Allergy Clin Immunol. Nov. 2014;134(5):1163-74.e16. Epub Jun. 17, 2014.
Steijns, J., & Hooijdonk, A.C., Occurrence, structure, biochemical properties and technological characteristics of lactoferrin. Br J Nutr. Nov. 2000;84 Suppl 1:S11-7.
Zavaleta et al., Efficacy of rice-based oral rehydration solution containing recombinant human lactoferrin and lysozyme in Peruvian children with acute diarrhea. J Pediatr Gastroenterol Nutr. Feb. 2007;44(2):258-64.
Zhang et al., Human lactoferrin in the milk of transgenic mice increases intestinal growth in ten-day-old suckling neonates. Adv Exp Med Biol. 2001;501:107-13.
International Search Report and Written Opinion dated Nov. 14, 2019 issued in corresponding International Patent Application No. PCT/US2019/046385.

\* cited by examiner

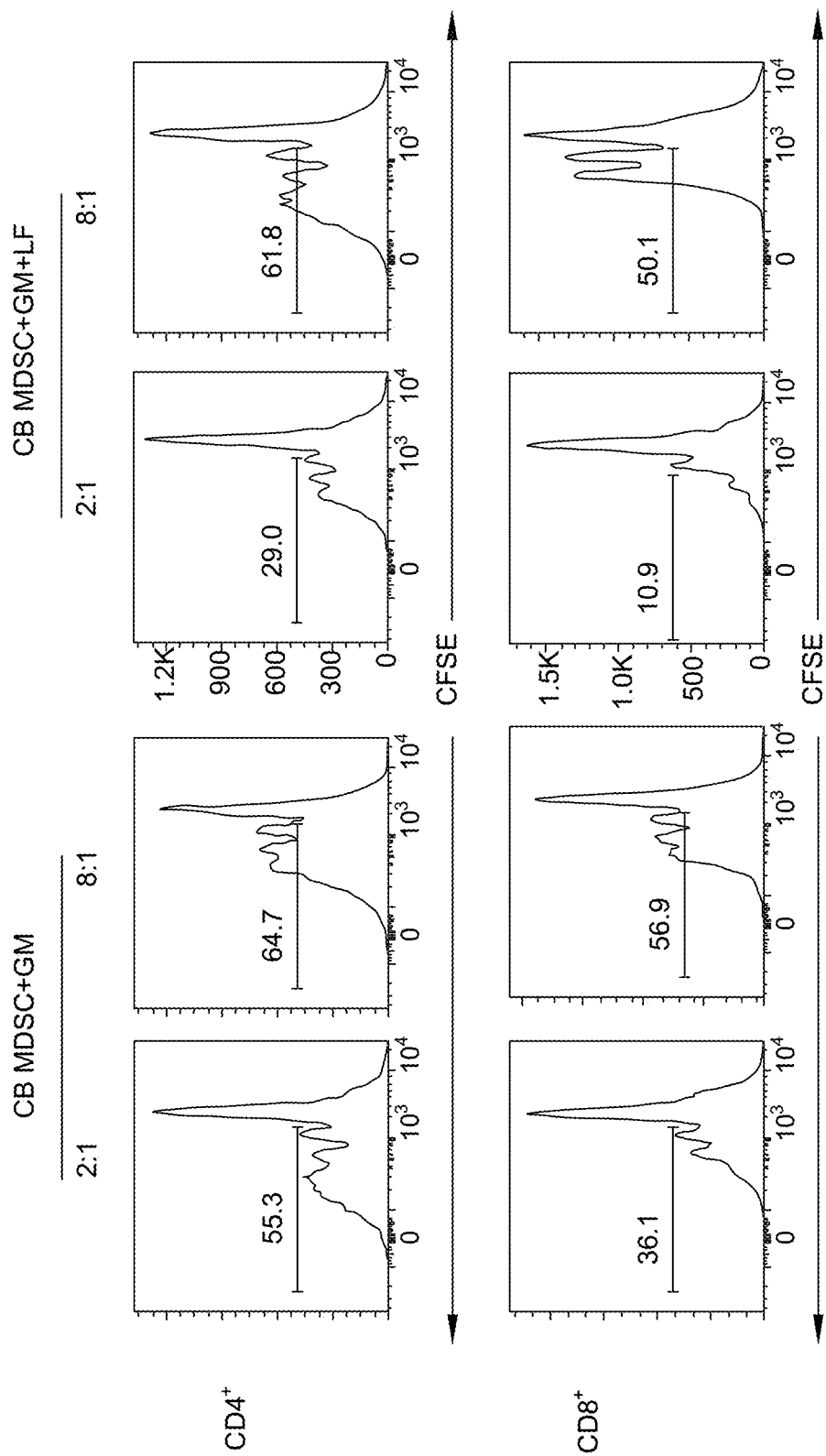
FIG. 3A(II)

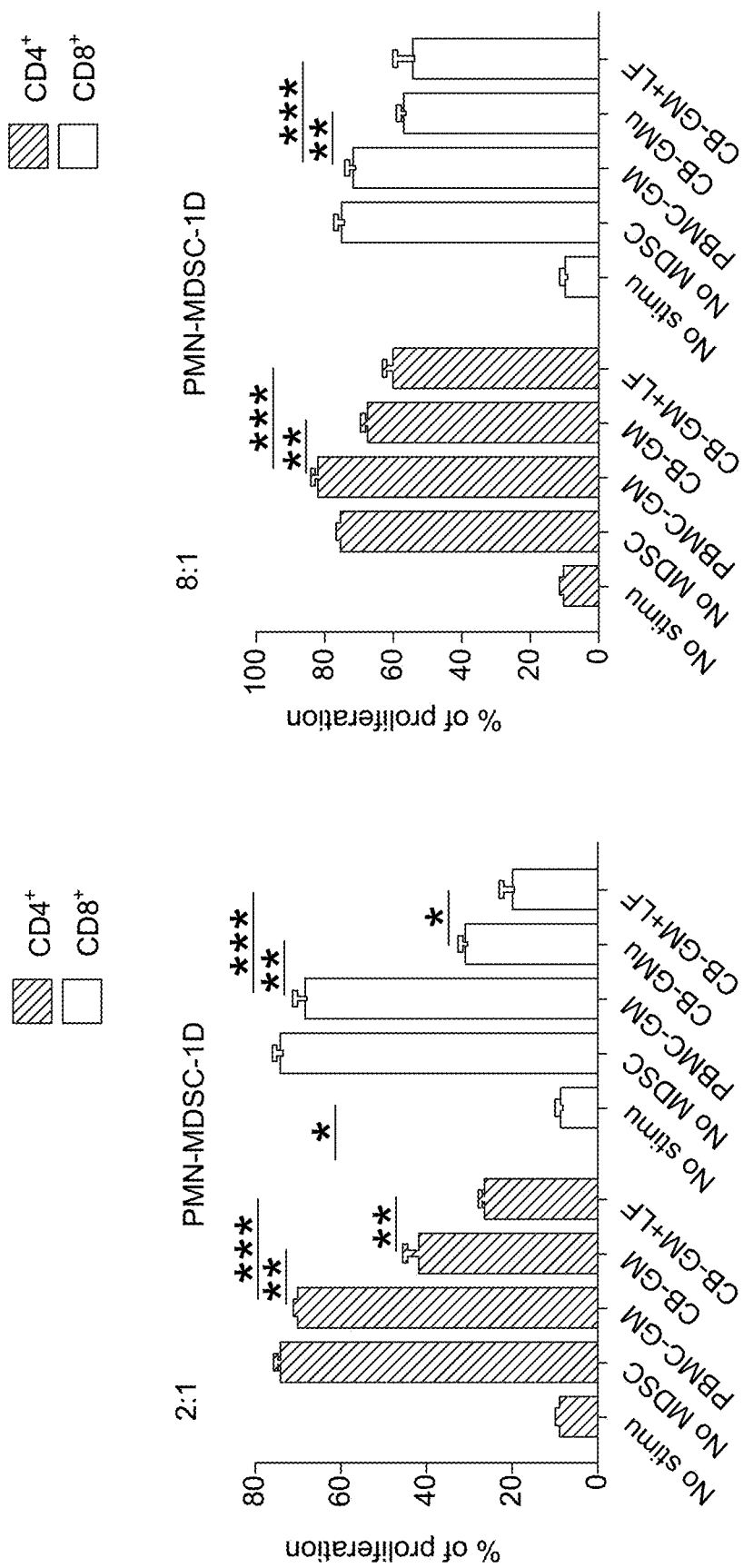
FIG. 3A(III)

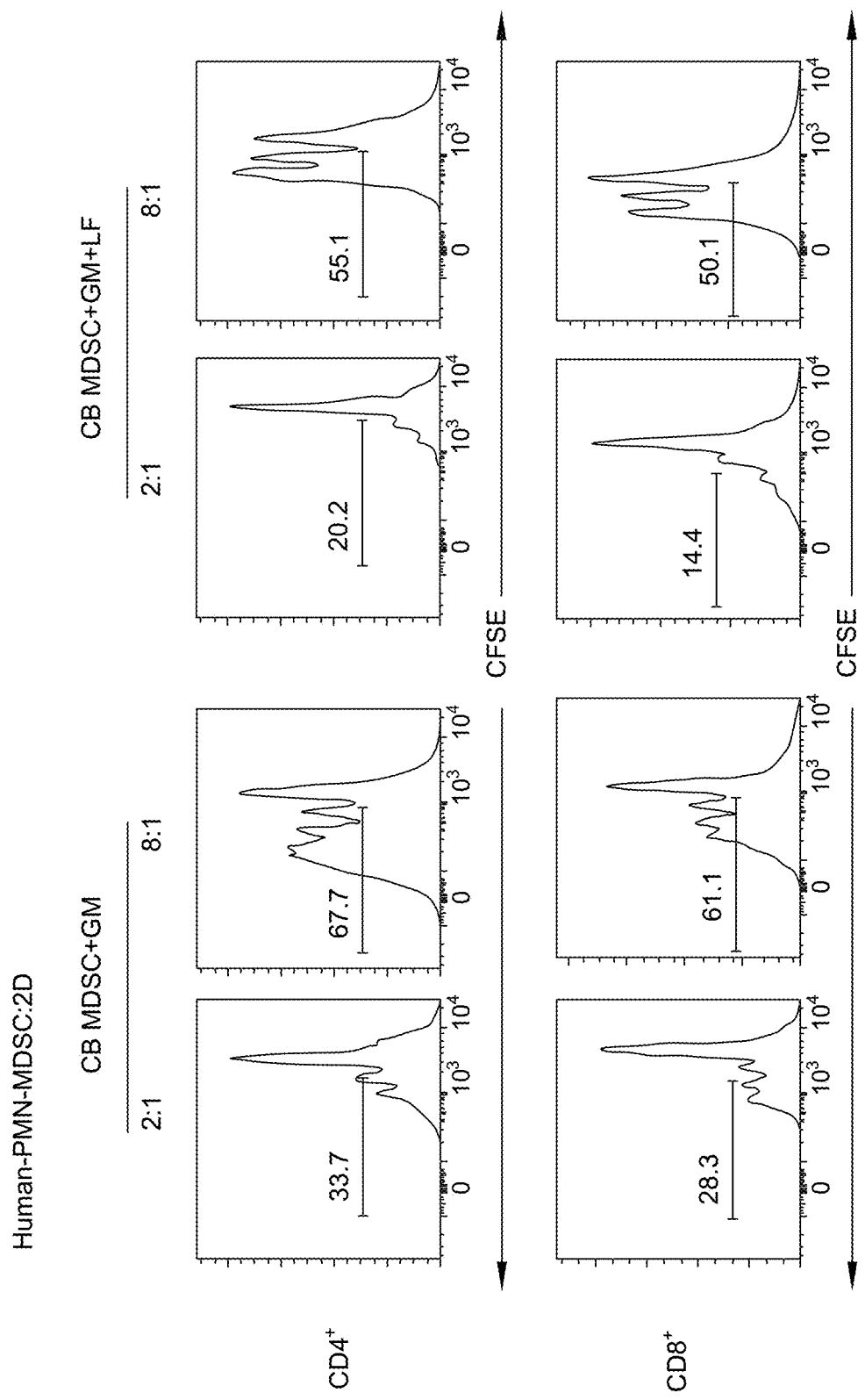
FIG. 3B(II)

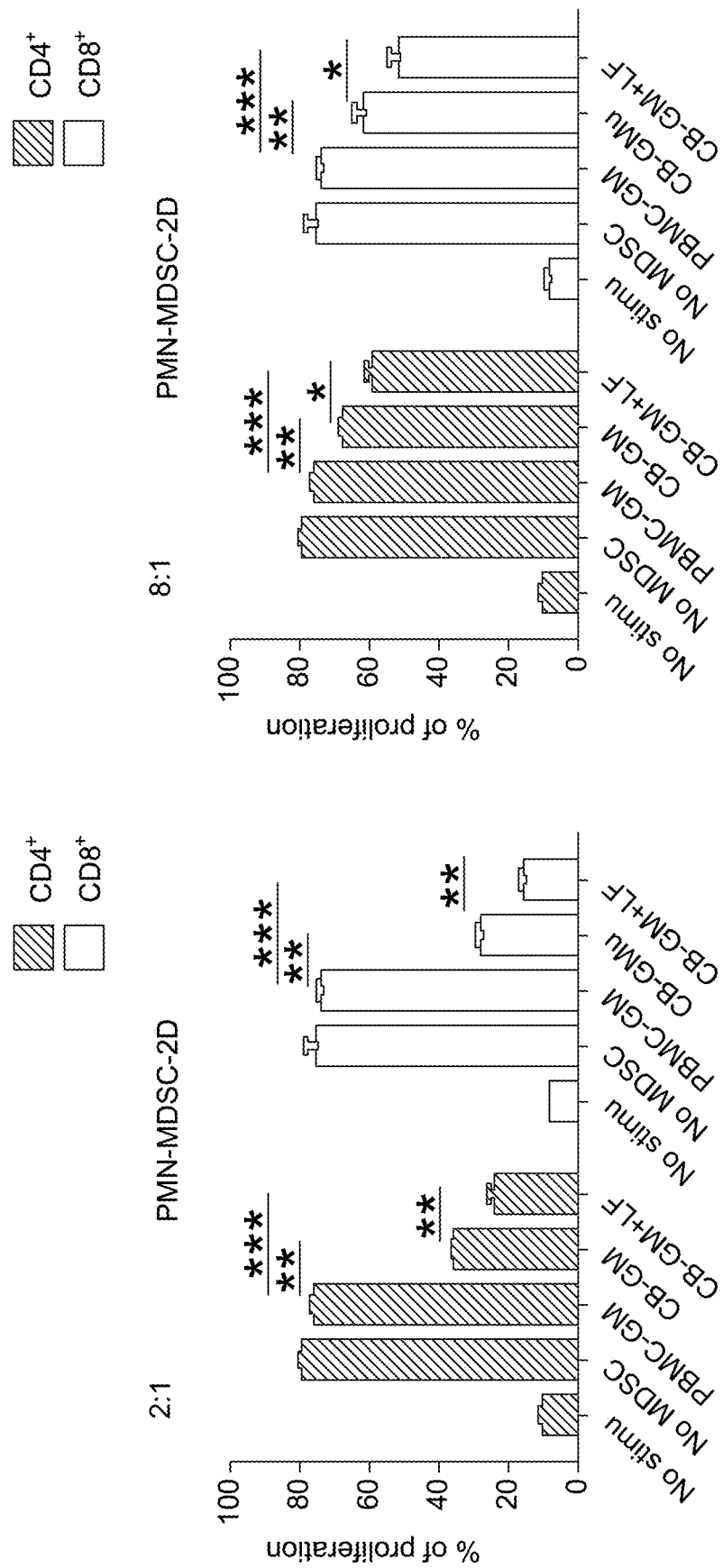
FIG. 3B(III)

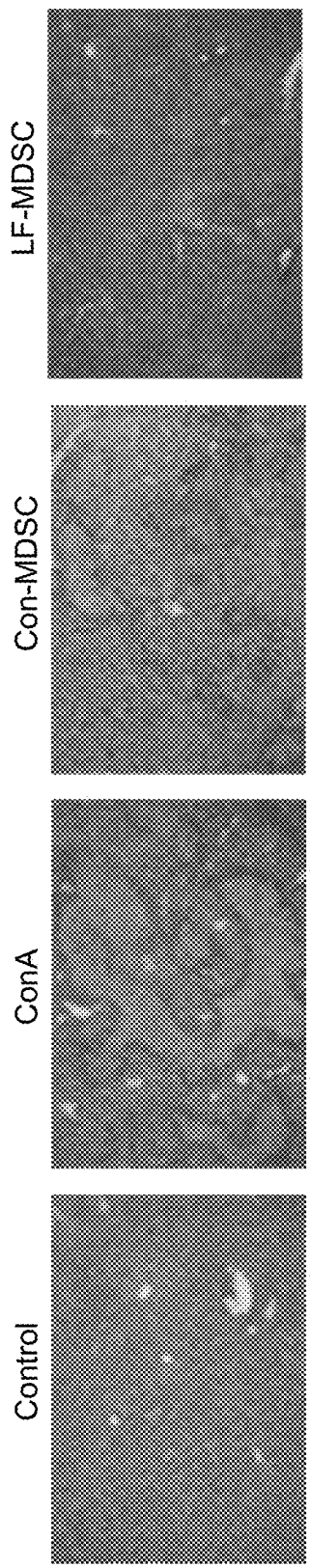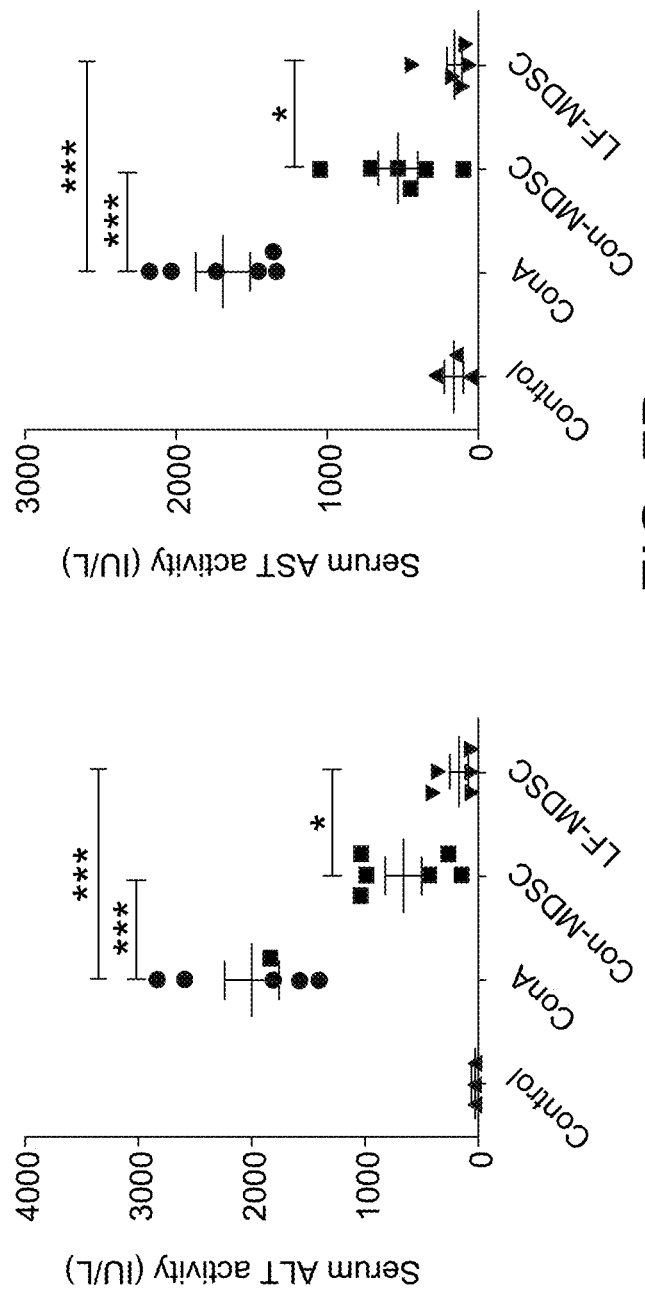
FIG. 7C
FIG. 7D

SEQUENCE LISTING

<160> NUMBER OF SEQ ID NOS: 12

<210> SEQ ID NO 1
<211> LENGTH: 711
<212> TYPE: PRT
<213> ORGANISM: Homo sapiens

<400> SEQUENCE: 1

Met Lys Leu Val Phe Leu Val Leu Leu Phe Leu Gly Ala Leu Gly Leu
1               5                   10                  15

Cys Leu Ala Gly Arg Arg Arg Arg Ser Val Gln Trp Cys Ala Val Ser

```
                    20                  25                  30
Gln Pro Glu Ala Thr Lys Cys Phe Gln Trp Gln Arg Asn Met Arg Arg
                35                  40                  45
Val Arg Gly Pro Pro Val Ser Cys Ile Lys Arg Asp Ser Pro Ile Gln
            50                  55                  60
Cys Ile Gln Ala Ile Ala Glu Asn Arg Ala Asp Ala Val Thr Leu Asp
 65                 70                  75                  80
Gly Gly Phe Ile Tyr Glu Ala Gly Leu Ala Pro Tyr Lys Leu Arg Pro
                85                  90                  95
Val Ala Ala Glu Val Tyr Gly Thr Glu Arg Gln Pro Arg Thr His Tyr
            100                 105                 110
Tyr Ala Val Ala Val Val Lys Lys Gly Gly Ser Phe Gln Leu Asn Glu
            115                 120                 125
Leu Gln Gly Leu Lys Ser Cys His Thr Gly Leu Arg Arg Asn Ala Gly
            130                 135                 140
Trp Asn Val Pro Ile Gly Thr Leu Arg Pro Phe Leu Asn Trp Thr Gly
145                 150                 155                 160
Pro Pro Glu Pro Ile Glu Ala Ala Val Ala Arg Phe Phe Ser Ala Ser
                165                 170                 175
Cys Val Pro Gly Ala Asp Lys Gly Gln Phe Pro Asn Leu Cys Arg Leu
            180                 185                 190
Cys Ala Gly Thr Gly Glu Asn Lys Cys Ala Phe Ser Ser Gln Glu Pro
            195                 200                 205
Tyr Phe Ser Tyr Ser Gly Ala Phe Lys Cys Leu Arg Asp Gly Ala Gly
            210                 215                 220
Asp Val Ala Phe Ile Arg Glu Ser Thr Val Phe Glu Asp Leu Ser Asp
225                 230                 235                 240
Glu Ala Glu Arg Asp Glu Tyr Glu Leu Leu Cys Pro Asp Asn Thr Arg
                245                 250                 255
Lys Pro Val Asp Lys Phe Lys Asp Cys His Leu Ala Arg Val Pro Ser
            260                 265                 270
His Ala Val Val Ala Arg Ser Val Asn Gly Lys Glu Asp Ala Ile Trp
            275                 280                 285
Asn Leu Leu Arg Gln Ala Gln Glu Lys Phe Gly Lys Asp Lys Ser Pro
        290                 295                 300
Lys Phe Gln Leu Phe Gly Ser Pro Ser Gly Gln Lys Asp Leu Leu Phe
305                 310                 315                 320
Lys Asp Ser Ala Ile Gly Phe Ser Arg Val Pro Pro Arg Ile Asp Ser
                325                 330                 335
Gly Leu Tyr Leu Gly Ser Gly Tyr Phe Thr Ala Ile Gln Asn Leu Arg
            340                 345                 350
Lys Ser Glu Glu Glu Val Ala Ala Arg Arg Ala Arg Val Val Trp Cys
            355                 360                 365
Ala Val Gly Glu Gln Glu Leu Arg Lys Cys Asn Gln Trp Ser Gly Leu
        370                 375                 380
Ser Glu Gly Ser Val Thr Cys Ser Ser Ala Ser Thr Thr Glu Asp Cys
385                 390                 395                 400
Ile Ala Leu Val Leu Lys Gly Glu Ala Asp Ala Met Ser Leu Asp Gly
                405                 410                 415
Gly Tyr Val Tyr Thr Ala Gly Lys Cys Gly Leu Val Pro Val Leu Ala
            420                 425                 430
Glu Asn Tyr Lys Ser Gln Gln Ser Ser Asp Pro Asp Pro Asn Cys Val
            435                 440                 445
```

```
Asp Arg Pro Val Glu Gly Tyr Leu Ala Val Ala Val Arg Arg Ser
    450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
                485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
        515                 520                 525

Gly Asp Glu Gln Gly Glu Asn Lys Cys Val Pro Asn Ser Asn Glu Arg
    530                 535                 540

Tyr Tyr Gly Tyr Thr Gly Ala Phe Arg Cys Leu Ala Glu Asp Ala Gly
545                 550                 555                 560

Asp Val Ala Phe Val Lys Gly Val Thr Val Leu Gln Asn Thr Asp Gly
                565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
        595                 600                 605

Cys His Leu Ala Met Ala Pro Asn His Ala Val Ser Arg Met Asp
    610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
                645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
        675                 680                 685

Ala Gly Ile Thr Asn Leu Lys Lys Cys Ser Thr Ser Pro Leu Leu Glu
    690                 695                 700

Ala Cys Glu Phe Leu Arg Lys
705                 710

<210> SEQ ID NO 2
<211> LENGTH: 33
<212> TYPE: PRT
<213> ORGANISM: Artificial Sequence
<220> FEATURE:
<223> OTHER INFORMATION: constructed sequence

<400> SEQUENCE: 2

Arg Arg Arg Arg Arg Arg Ser Val Gln Trp Cys Ala Val Ser Gln Pro
1               5                   10                  15

Glu Ala Thr Lys Cys Phe Gln Trp Gln Arg Asn Met Arg Lys Arg Arg
                20                  25                  30

Arg

<210> SEQ ID NO 3
<211> LENGTH: 33
<212> TYPE: PRT
<213> ORGANISM: Artificial Sequence
<220> FEATURE:
<223> OTHER INFORMATION: constructed sequence

<400> SEQUENCE: 3
```

```
Arg Arg Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Arg Arg
            20                  25                  30

Arg
```

<210> SEQ ID NO 4
<211> LENGTH: 30
<212> TYPE: PRT
<213> ORGANISM: Artificial Sequence
<220> FEATURE:
<223> OTHER INFORMATION: constructed sequence

<400> SEQUENCE: 4

```
Arg Arg Arg Arg Arg Arg Ser Val Gln Trp Cys Ala Val Ser Gln Pro
1               5                   10                  15

Glu Ala Thr Lys Cys Phe Gln Trp Gln Arg Asn Met Arg Lys
            20                  25                  30
```

<210> SEQ ID NO 5
<211> LENGTH: 33
<212> TYPE: PRT
<213> ORGANISM: Artificial Sequence
<220> FEATURE:
<223> OTHER INFORMATION: constructed sequence

<400> SEQUENCE: 5

```
Arg Arg Arg Arg Arg Arg Ser Val Gln Trp Gln Ala Val Ser Gln Pro
1               5                   10                  15

Ile Ala Thr Glu Gln Phe Gln Trp Gln Arg Asn Met Arg Lys Arg Arg
            20                  25                  30

Arg
```

<210> SEQ ID NO 6
<211> LENGTH: 33
<212> TYPE: PRT
<213> ORGANISM: Artificial Sequence
<220> FEATURE:
<223> OTHER INFORMATION: constructed sequence

<400> SEQUENCE: 6

```
Arg Arg Arg Arg Arg Arg Ser Val Gln Trp Ala Ala Val Ser Gln Pro
1               5                   10                  15

Ile Ala Thr Glu Ala Phe Gln Trp Gln Arg Asn Met Arg Lys Arg Arg
            20                  25                  30

Arg
```

<210> SEQ ID NO 7
<211> LENGTH: 33
<212> TYPE: PRT
<213> ORGANISM: Artificial Sequence
<220> FEATURE:
<223> OTHER INFORMATION: constructed sequence

<400> SEQUENCE: 7

```
Arg Arg Arg Arg Arg Arg Ser Val Gln Trp Gln Ala Val Ser Gln Pro
1               5                   10                  15

Glu Ala Thr Lys Gln Phe Gln Trp Gln Arg Asn Met Arg Lys Arg Arg
            20                  25                  30

Arg
```

<210> SEQ ID NO 8
<211> LENGTH: 33
<212> TYPE: PRT
<213> ORGANISM: Artificial Sequence
<220> FEATURE:
<223> OTHER INFORMATION: constructed sequence

<400> SEQUENCE: 8

Arg Arg Arg Arg Arg Arg Ser Val Gln Trp Gln Ala Val Ser Gln Pro
1               5                   10                  15

Gly Ala Thr Lys Gln Phe Gln Trp Gln Arg Asn Met Arg Lys Arg Arg
            20                  25                  30

Arg

<210> SEQ ID NO 9
<211> LENGTH: 33
<212> TYPE: PRT
<213> ORGANISM: Artificial Sequence
<220> FEATURE:
<223> OTHER INFORMATION: constructed sequence

<400> SEQUENCE: 9

Arg Arg Arg Arg Arg Arg Ser Val Gln Trp Gln Ala Val Ser Gln Pro
1               5                   10                  15

Ile Ala Thr Lys Gln Phe Gln Trp Gln Arg Asn Met Arg Lys Arg Arg
            20                  25                  30

Arg

<210> SEQ ID NO 10
<211> LENGTH: 33
<212> TYPE: PRT
<213> ORGANISM: Artificial Sequence
<220> FEATURE:
<223> OTHER INFORMATION: constructed sequence

<400> SEQUENCE: 10

Arg Arg Arg Arg Arg Arg Ser Val Gln Trp Gln Ala Val Ser Gln Pro
1               5                   10                  15

Gln Ala Thr Gly Gln Phe Gln Trp Gln Arg Asn Met Arg Lys Arg Arg
            20                  25                  30

Arg

<210> SEQ ID NO 11
<211> LENGTH: 33
<212> TYPE: PRT
<213> ORGANISM: Artificial Sequence
<220> FEATURE:
<223> OTHER INFORMATION: constructed sequence

<400> SEQUENCE: 11

Arg Arg Arg Arg Arg Arg Ser Val Gln Trp Gln Ala Val Ser Gln Pro
1               5                   10                  15

Ile Ala Thr Ile Gln Phe Gln Trp Gln Arg Asn Met Arg Lys Arg Arg
            20                  25                  30

Arg

<210> SEQ ID NO 12
<211> LENGTH: 33
<212> TYPE: PRT
<213> ORGANISM: Artificial Sequence
<220> FEATURE:
<223> OTHER INFORMATION: constructed sequence

```
<400> SEQUENCE: 12

Arg Arg Arg Arg Arg Arg Ser Val Gln Trp Ala Ala Val Ser Gln Pro
1               5                   10                  15

Ile Ala Thr Lys Ala Phe Gln Trp Gln Arg Asn Met Arg Lys Arg Arg
            20                  25                  30

Arg
```

USE OF LACTOFERRIN FOR GENERATING MYELOID-DERIVED SUPPRESSOR CELLS

CROSS-REFERENCE TO RELATED APPLICATIONS

This is National Stage Entry under 35 U.S.C. 371 of International Patent Application No. PCT/US2019/046385, filed Aug. 13, 2019, which claims the benefit under 35 USC 119 (e) of U.S. Provisional Patent Application Nos. 62/758,125 and 62/758,128, both filed Nov. 9, 2018. These applications are incorporated by reference herein.

STATEMENT REGARDING FEDERALLY SPONSORED RESEARCH OR DEVELOPMENT

This invention was made with government support under Grant No. CA010815 awarded by the National Institutes of Health. The government has certain rights in the invention.

SEQUENCE LISTING

The instant application contains a Sequence Listing which has been submitted electronically in ASCII format and is hereby incorporated by reference in its entirety. Said electronic copy, created on Aug. 13, 2019, is named WST175PCT_Seq-Listing, and is 11 kb.

BACKGROUND

Myeloid-derived suppressor cells (MDSCs) are a heterogeneous population of cells that expands during cancer, inflammation and infection, and that has a remarkable ability to suppress T-cell responses. These cells constitute a unique component of the immune system that regulates immune responses in healthy individuals and in the context of various diseases.

MDSCs represent an intrinsic part of the myeloid-cell lineage and are a heterogeneous population that is comprised of myeloid-cell progenitors and precursors of myeloid cells. In healthy individuals, immature myeloid cells (IMCs) generated in bone marrow quickly differentiate into mature granulocytes, macrophages or dendritic cells (DCs). In pathological conditions such as cancer, various infectious diseases, sepsis, trauma, bone marrow transplantation or some autoimmune disorders, a partial block in the differentiation of IMCs into mature myeloid cells results in an expansion of this population. Importantly, the activation of these cells in a pathological context results in the unregulated expression of immune suppressive factors such as arginase (encoded by ARG1) and inducible nitric oxide synthase (iNOS; also known as NOS2) and an increase in the production of NO (nitric oxide) and reactive oxygen species (ROS). Together, this results in the expansion of an IMC population that has immune suppressive activity; these cells are now collectively known as MDSCs.

Inflammation is one of the most complicated processes in the human body, and the promoting and inhibiting mechanisms controlling them are significant players in the pathogenesis of various diseases. MDSCs have been implicated in the pathogenesis of various inflammatory conditions including asthma (Shi et al, Myeloid-derived suppressor cell function is diminished in aspirin-triggered allergic airway hyperresponsiveness in mice, J Allergy Clin Immunol November 2014; 134:1163-74); non-neoplastic inflamed organs (Sendo et al, Myeloid-derived suppressor cells in nonneoplastic inflamed organs, Inflammation and Regeneration (2018) 38:19); and hepatic inflammation and fibrosis (Hammerich and Tacke, Emerging roles of myeloid derived suppressor cells in hepatic inflammation and fibrosis, World J Gastrointest Pathophysiol. 2015 Aug. 15; 6(3):43-50). Although initial observations and most of the current information regarding the role of MDSCs in immune responses has come from studies in the cancer field, accumulating evidence has shown that MDSCs also regulate immune responses in bacterial and parasitic infections, acute and chronic inflammation, traumatic stress, surgical sepsis and transplantation.

What is needed in the art is more effective treatment for inflammatory conditions.

SUMMARY OF THE INVENTION

Provided herein, in one aspect is a method of generating MDSCs ex vivo. The method includes culturing blood cells with lactoferrin. In one embodiment, the blood cells are selected from peripheral blood mononuclear cells, cord blood, and bone marrow cells.

In another aspect, a pharmaceutical composition comprising the MSDCs produced by the methods described herein is provided.

In yet another aspect, a method of treating an inflammatory disease in a subject in need thereof is provided. In another aspect, a method of preventing, reducing the likelihood of occurrence or severity of an inflammatory disease in a subject in need thereof is provided. These methods include administering a pharmaceutical composition which includes MDSCs as described herein. In another embodiment, method includes administering lactoferrin to the subject.

In yet another aspect, a method of generating MDSCs in vivo is provided. The method includes administering lactoferrin to a subject in need thereof.

In some embodiments, the inflammatory condition is an autoimmune disease. In some embodiments, the subject is a child. In one embodiment, the inflammatory disease is necrotizing enterocolitis (NEC).

Other aspects and advantages of the invention will be readily apparent from the following detailed description of the invention.

DESCRIPTION OF THE FIGURES

FIG. 5A: Experimental Design. Enriched G-MDSCs (2 million) from BM culture in the presence of GM-CSF, IL-6, without or with LF treatment were injected into recipient mice via the tail vein. Four groups were included: Control Water), DSS+PBS (PBS), DSS+ control-derived MDSC (Con-MDSC, without LF), DSS+LF-derived MDSC (LF-MDSC, with LF). FIG. 5B: Colon HE staining. FIG. 5C: Colon length (mm). FIG. 5D: Weight loss. FIG. 5E: Disease activity index. FIG. 5F: Histology score.

FIG. 6A. The experimental design. Enriched G-MDSCs (3 million) from BM culture in the presence of GM-CSF, IL-6, without or with LF treatment were injected into recipient mice via the tail vein1 day before each sensitization. Four groups were included: Control (No treatments), OVA+PBS (PBS), OVA+control-derived MDSC (Con-MDSC, without LF), OVA+LF-derived MDSC (LF-MDSC, with LF). FIG. 6B. Lung HE staining. FIG. 6C. Inflammation score and BAL cell count. FIG. 6D. IgE and IL-4 level in BAL. FIG. 6E. Eosinophile granulocyte percentage and IL-13 level in BAL.

FIG. 7A-FIG. 7E demonstrate that LTF-derived MDSCs attenuates hepatitis induced by Con A. FIG. 7A. The experimental design. Enriched G-MDSCs (3 million) from BM culture in the presence of GM-CSF, IL-6, without or with LF treatment were injected into recipient mice via the tail vein1 day before Con A injection. Four groups were included: Control (No treatment), OVA+PBS (PBS), OVA+control-derived MDSC (Con-MDSC, without LF), OVA+LF-derived MDSC (LF-MDSC, with LF). FIG. 7B. Th1 and Treg cells numbers. FIG. 7C. Liver HE staining. FIG. 7D. ALT and AST level of plasma. FIG. 7E. mRNA level of IFN-γ, TNF-a, IL6 of Liver tissue.

DETAILED DESCRIPTION OF THE INVENTION

Figure 1A:
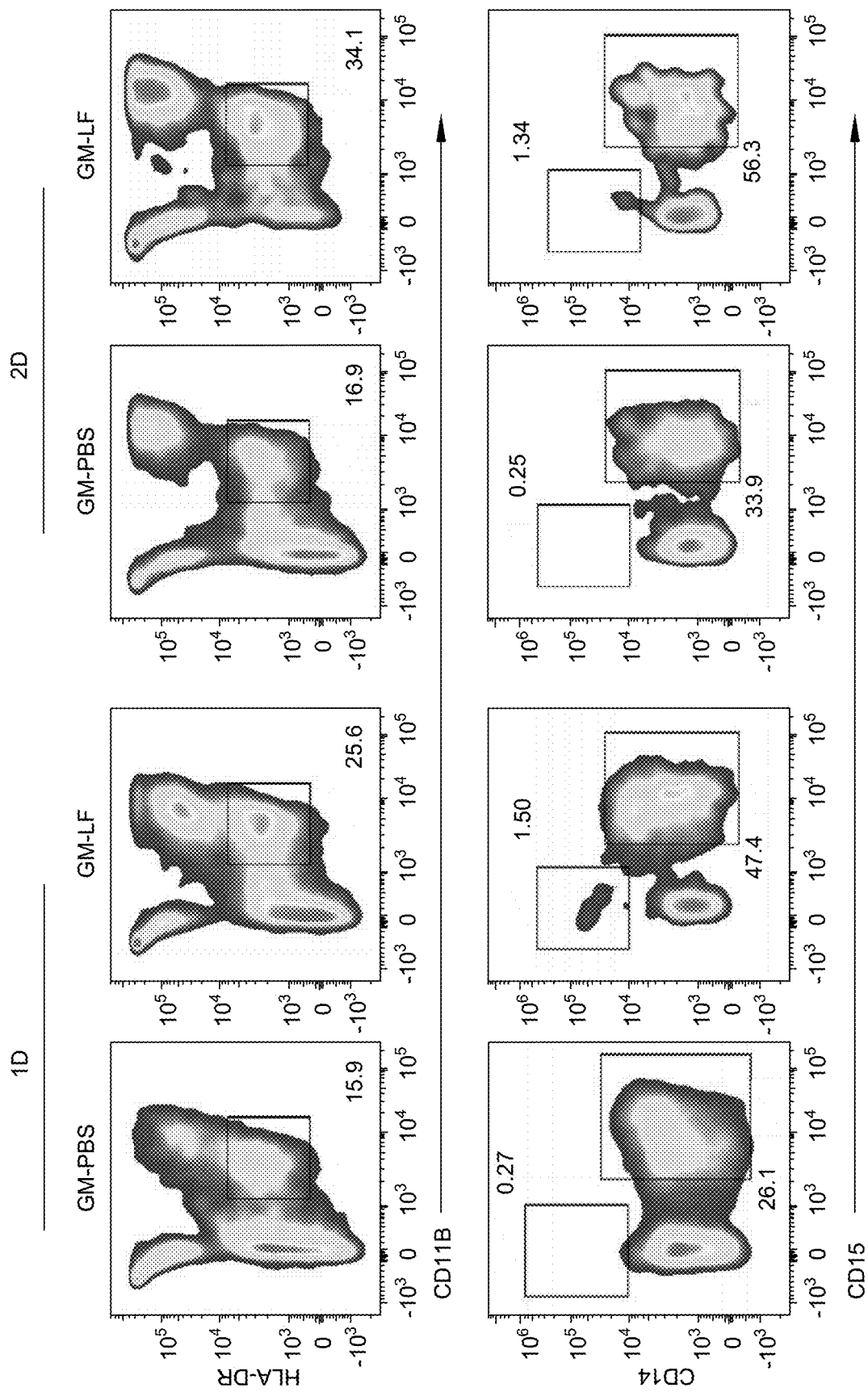
FIG. 1. PBMC from cord blood were cultured with GM-CSF and lactoferrin (LF) for 1 day or 2 days and the proportion of neutrophils (PMN-MDSC) and monocytes (M-MDSC) was evaluated. Top panel—typical representation of the results. Bottom panel—cumulative results from individual experiments. Data depict accumulation of PMN-MDSC in LF treated cells.
Figure 1B:
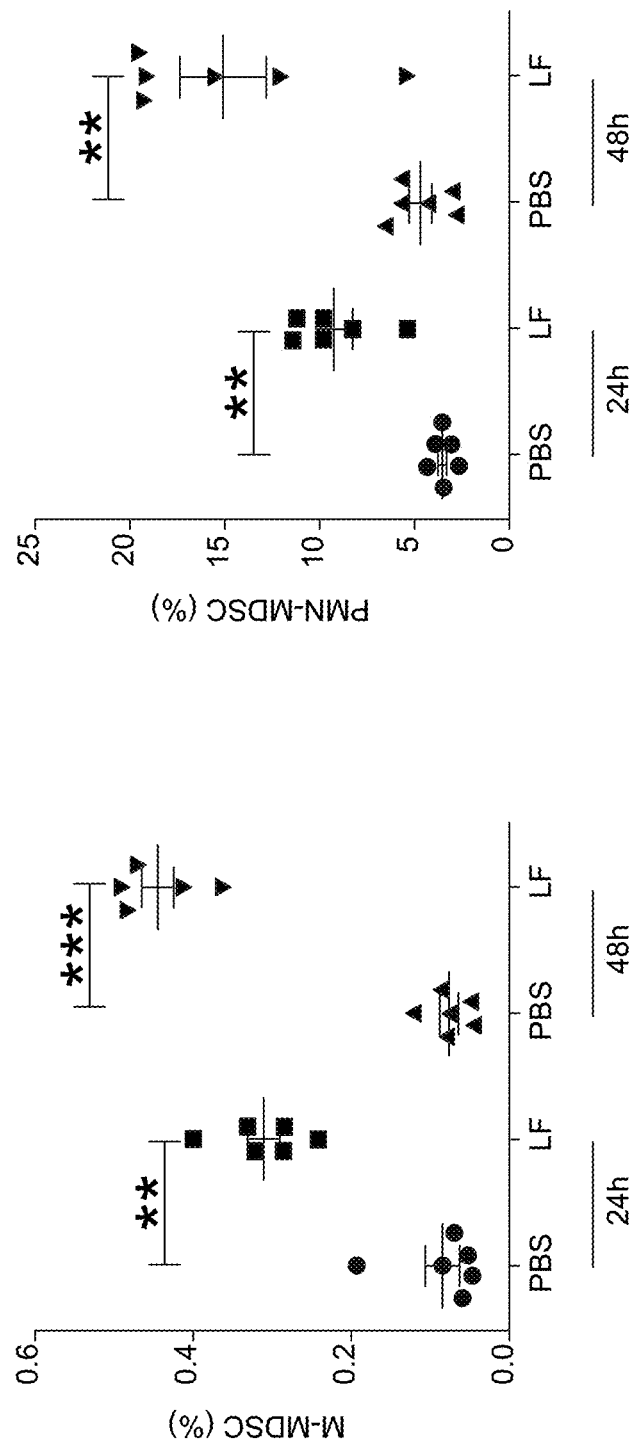
Figure 2A:
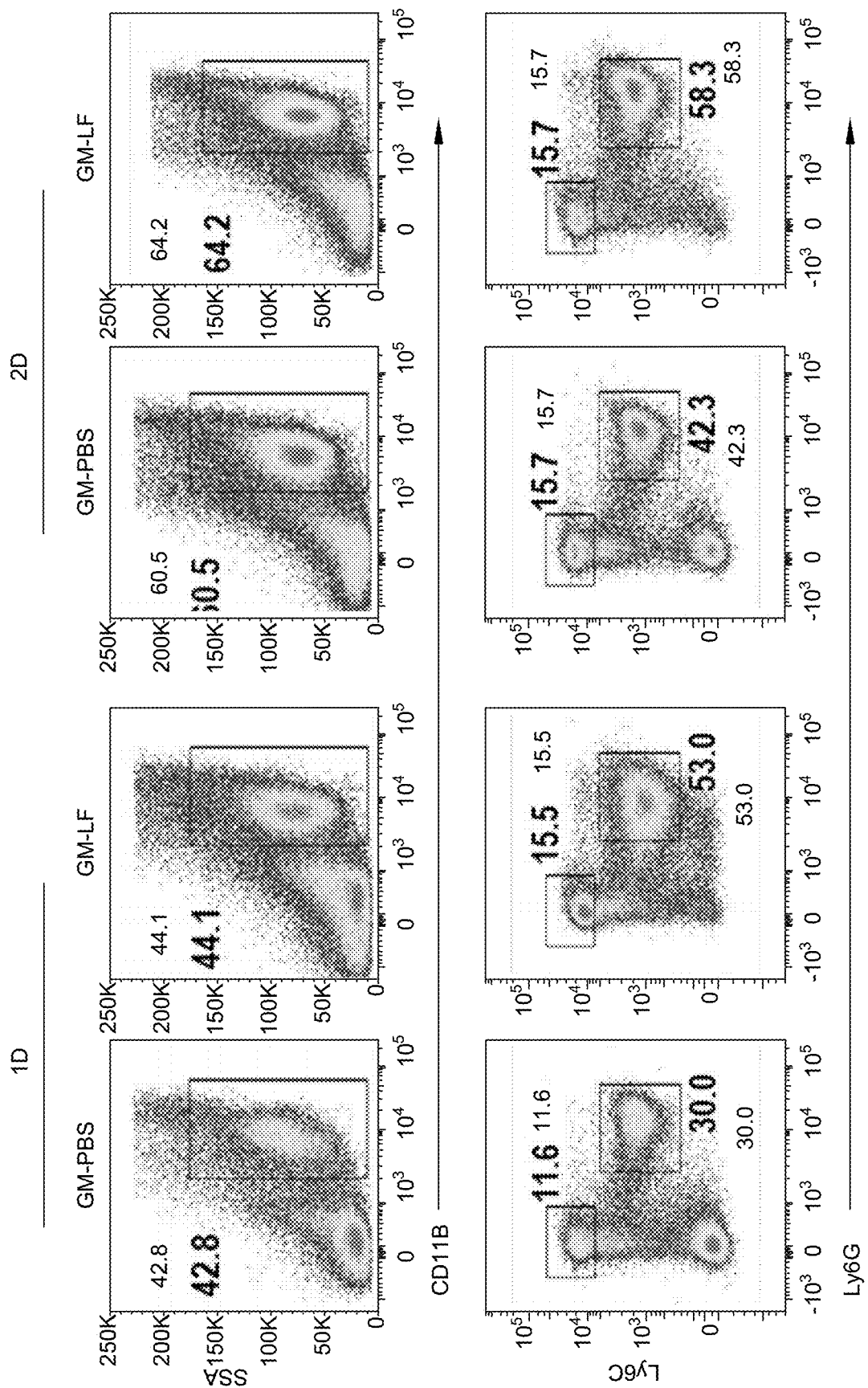
FIG. 2. Experimental conditions of FIG. 1 were replicated with cells isolated from bone marrow of mice.
Figure 2B:
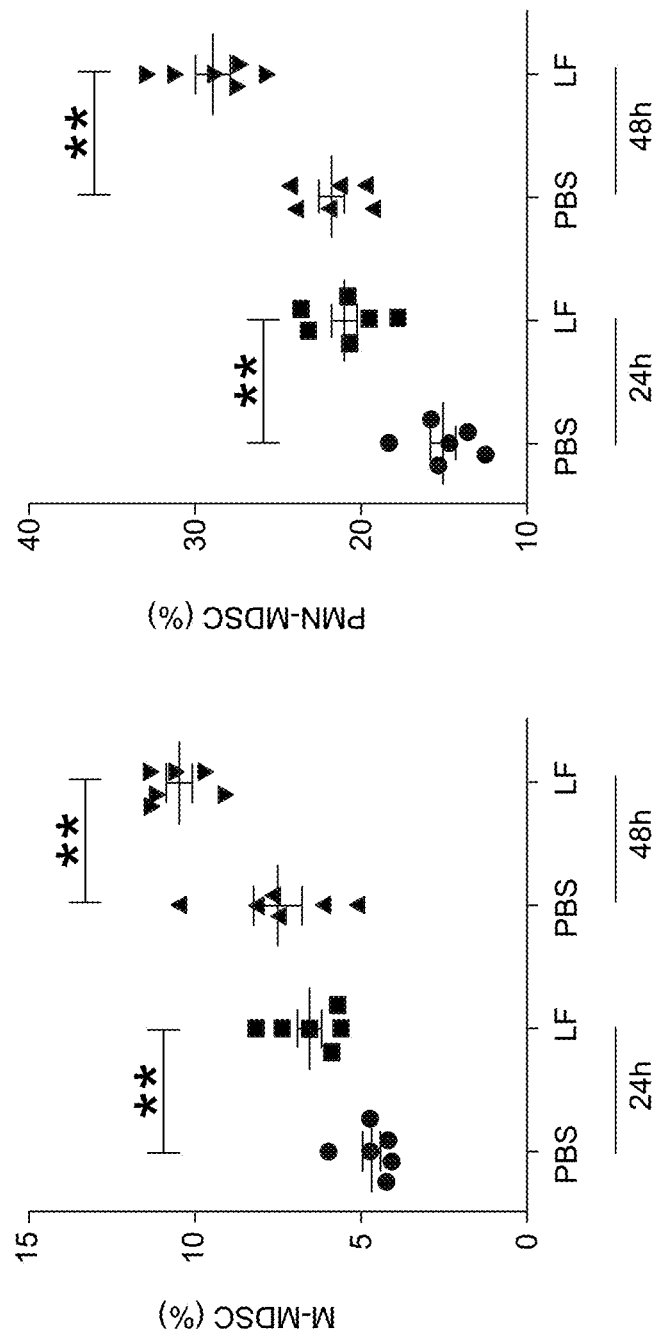

Myeloid-derived suppressor cells (MDSCs) have been implicated in the pathogenesis of inflammatory disease and the inventors have demonstrated that administration of MDSCs are useful in treating certain inflammatory conditions. As described herein, the inventors have shown that culturing certain blood cells with lactoferrin results in generation and expansion of MDSCs. In addition, the inventors have shown that administering lactoferrin to subjects in need thereof results in generation and expansion of MDSCs in vivo.

It is to be noted that the term "a" or "an" refers to one or more. As such, the terms "a" (or "an"), "one or more," and "at least one" are used interchangeably herein.

While various embodiments in the specification are presented using "comprising" language, under other circumstances, a related embodiment is also intended to be interpreted and described using "consisting of" or "consisting essentially of" language. The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

The term "regulation" or variations thereof as used herein refers to the ability of a compound of formula (I) to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla. In one embodiment, the subject is a human. The subject may be of any age, as determined by the health care provider. In one embodiment, the subject is a child, i.e., under the age of 18 years old. In another embodiment, the subject is a young child, i.e., 8 years old or less. In another embodiment, the subject is a toddler, i.e., 3 years old or less. In yet another embodiment, the subject is an infant, i.e., 1 year of age or less. In yet another embodiment, the subject is a newborn or neonate, i.e., one month of age or less. In another embodiment, the subject is a preterm infant.

Lactoferrin (LF) is an iron-binding protein that is secreted by serous epithelial cells and neutrophils that competes with bacteria for iron, thereby inhibiting bacterial growth. LF is expressed in most biological fluids with particularly high levels in mammalian milk. LF can bind and sequester lipopolysaccharides (LPS), thus preventing pro-inflammatory pathway activation, sepsis and tissue damages. LF is also considered a cell-secreted mediator that bridges the innate and adaptive immune responses. See, WO 2017/044979, which is incorporated herein by reference. Lactoferrin is a single-chain iron-binding glycoprotein of approximately 80 kDa that belongs to the human family of transferrins. LF is present in myriad mucosal fluids, but is most predominant in human milk, particularly in the colostrum during early lactation, where it has been suggested to promote the healthy growth and development of the GI tract (Zhang, et al, 2001, Adv. Exp. Med. Biol. 501:107-13), promote the growth of commensal bacterial populations and protect against the establishment of pathogenic bacteria and viruses (Barboza, et al, 2012, Mol. Cell. Proteomics 11:M111 015248; Ochoa, T. J. and Cleary, T. G., 2009, Biochimie 91:30-4; Ammendolia, et al, 2012, Pathog. Glob. Health 106: 12-9). Human colostrums and mature breast milk contain 5.8 mg/mL and 3.3 mg/mL of LF, respectively (Montagne, et al, 1999, J. Pediatr. Gastroenterol. Nutr. 29:75-80; Montagne, et al, 2001, Adv. Exp. Med. Biol. 501:241-7). In contrast, bovine colostrum and milk contain markedly reduced concentrations of LF (1.5 mg/mL in colostral whey and 20-200 µg/mL in milk) (Steijns, et al, 2000, Br. J. Nutr., 84 Suppl. LS11-7). LF has been previously identified for its multifactorial and beneficial activities in several models of human health including inflammation (Mueller, et al, 2011, Curr. Med. Res. Opin. 27:793-7; Zavaleta, et al, 2007, J. Pediatr. Gastroenterol. Nutr. 44:258-64), wound healing (Lyons, et al, 2007, Am. J. Surg. 193:49-54), infectious diseases (Zavaleta, et al, 2007, J. Pediatr. Gastroenterol. Nutr. 44:258-64; King, et al, 2007, J. Pediatr. Gastroenterol. Nutr. 44:245-51; Ochoa, et al, 2008, Clin. Infect. Dis. 46: 1881-3) and cancer (Parikh, et al, 2011, J. Clin. Oncol. 29:4129-36; Hayes, et al, 2010, Invest. New Drugs 28: 156-62). LF has been described for modulation of T cell phenotype in subjects having neurodegenerative or autoimmune disease (WO 2017/044979, which is incorporated herein by reference).

As used herein, the term "lactoferrin" or "lactoferrin composition" refers to any native lactoferrin and any analog, modification, derivative or fragment thereof. The source of the lactoferrin may be human, or another mammal such as non-human primate, bovine, ovine, porcine, caprine, or murine. In one embodiment, the lactoferrin is a human lactoferrin. In one embodiment, the lactoferrin is the human lactoferrin found at UniProtKB-Q5EK51 (SEQ ID NO: 1).

```
                                          SEQ ID NO: 1
          10         20         30         40
 MKLVFLVLLF LGALGLCLAG RRRRSVQWCA VSQPEATKCF
```

-continued

```
         50          60          70          80
    QWQRNMRRVR  GPPVSCIKRD  SPIQCIQAIA  ENRADAVTLD 90         100         110         120
    GGFIYEAGLA  PYKLRPVAAE  VYGTERQPRT  HYYAVAVVKK 130         140         150         160
    GGSFQLNELQ  GLKSCHTGLR  RNAGWNVPIG  TLRPFLNWTG 170         180         190         200
    PPEPIEAAVA  RFFSASCVPG  ADKGQFPNLC  RLCAGTGENK 210         220         230         240
    CAFSSQEPYF  SYSGAFKCLR  DGAGDVAFIR  ESTVFEDLSD 250         260         270         280
    EAERDEYELL  CPDNTRKPVD  KFKDCHLARV  PSHAVVARSV 290         300         310         320
    NGKEDAIWNL  LRQAQEKFGK  DKSPKFQLFG  SPSGQKDLLF 330         340         350         360
    KDSAIGFSRV  PPRIDSGLYL  GSGYFTAIQN  LRKSEEEVAA 370         380         390         400
    RRARVVWCAV  GEQELRKCNQ  WSGLSEGSVT  CSSASTTEDC 410         420         430         440
    IALVLKGEAD  AMSLDGGYVY  TAGKCGLVPV  LAENYKSQQS 450         460         470         480
    SDPDPNCVDR  PVEGYLAMAV  VRRSDTSLTW  NSVKGKKSCH 490         500         510         520
    TAVDRTAGWN  IPMGLLFNQT  GSCKFDEYFS  QSCAPGSDPR 530         540         550         560
    SNLCALCIGD  EQGENKCVPN  SNERYYGYTG  AFRCLAEDAG 570         580         590         600
    DVAFVKGVTV  LQNTDGNNNE  AWAKDLKLAD  FALLCLDGKR 610         620         630         640
    KPVTEARSCH  LAMAPNHAVV  SRMDKVERLK  QVLLHQQAKF 650         660         670         680
    GRNGSDCPDK  FCLFQSETKN  LLFNDNTECL  ARLHGKTTYE 690         700         710
    KYLGPQYVAG  ITNLKKCSTS  PLLEACEFLR  K
```

The term lactoferrin also includes the following compounds found in Table 1. Each of these publications is incorporated herein by reference.

TABLE 1

| Lactoferrin compounds | | |
|---|---|---|
| Patent, Application, or Publication Number | Drug name(s) | Description from claims or specification |
| U.S. Pat. No. 6,066,469A | human lactoferrin, recombinant human lactoferrin | human lactoferrin, recombinant human lactoferrin |
| U.S. Pat. No. 6,455,687B1 | human lactoferrin clone, recombinant human lactoferrin clone | human lactoferrin clone, recombinant human lactoferrin clone |
| U.S. Pat. No. 7,420,033 | lactoferrin peptide (33-mer) | A pharmaceutical composition comprising a lactoferrin related peptide (33-mer peptides) |
| U.S. Pat. No. 7,183,381 | talactoferrin alfa | A pharmaceutical composition comprising a lactoferrin related peptide; an isolated polypeptide having an amino acid sequence as defined in SEQ ID NO: 10 (lactoferrin related peptide sequence) |
| U.S. Pat. No. 6,111,081A | lactoferrin variants | Lactoferrin variants, nucleic acid sequences encoding a lactoferrin variant |
| U.S. Pat. No. 6,569,831B1 | VEN-100, VEN-120, VEN-150 | A recombinant nucleic acid molecule encoding a mature lactoferrin or a lactoferrin-derived protein; a recombinant vector comprising a recombinant nucleic acid molecule encoding a mature lactoferrin or a lactoferrin-derived protein |
| U.S. Pat. No. 7,354,902 | | A mature lactoferrin obtained by a method of producing lactoferrin |
| WO2002064750A2 | | heterologous lactoferrin polypeptide produced in a grain of a plant; codon optimized nucleic acid molecule for expression of polypeptides in monocot, wherein the nucleic acid is a human lactoferrin nucleic acid encoding human lactoferrin |
| WO2017044979A2 | recombinant human lactoferrin (rhLF) | Pharmaceutical composition comprising plant-derived recombinant human lactoferrin |
| EP2668205B1 | PXL-01 | Peptides comprising mature human lactoferrin amino acid sequences |
| U.S. Pat. No. 7,253,143B1 | | purified lactoferrin peptides |
| US20110053833A1 | | Synthetic peptides which can be used for same purposes as lactoferrin, lactoferricin or other lactoferrin derived peptides |
| U.S. Pat. No. 8,815,812B2 | | Isolated peptides and synthetic peptides which can be used for the same purposes as in US20110053833A1 (above) |
| U.S. Pat. No. 8,673,839 JP5427170 | polyethylene glycol-lactoferrin (PEG-lactoferrin) | A biologically active complex of lactoferrin Biologically active complex of lactoferrin and PEG |
| EP2030980A1 | hLF-111 (also known as hLF 1-11, hLF 111, hLF1-11, hLF111, Human Lactoferrin Peptide 1-11, Human Lactoferrin | mutants of lactoferrin (polypeptides) |
| 15/847,719 US20180127486A1 | PRC-14, PRC14 | recombinant polypeptide comprising lactoferrin (clinical trial by pharmareview corp |

TABLE 1-continued

Lactoferrin compounds

| Patent, Application, or Publication Number | Drug name(s) | Description from claims or specification |
|---|---|---|
| CN105664174A | Lf-HA-DOX | preclinical dev for treatment of intracerebral hemmorage) Lf-HA-DOX macromolecule prodrug compound |
| US20140357550A1 | AdeLact | pharmaceutical composition with sustained and rapidly commencing antitoxic effect, based on nanostructures, producing human lactoferrin directly in the body |
| WO2008003688A1 | ALX-009 (Meveol - brand name) | combination of hypothiocyanite (OSCN-) and lactoferrin (used in clinical trial through inhalation for treatment of CF) |

In one embodiment, the lactoferrin is a lactoferrin derived peptide, such as

```
                                   (SEQ ID NO: 2)
RRRRRRSVQW CAVSQPEATK CFQWQRNMRK RRR;

(SEQ ID NO: 3)
RRRRRSVQWC AVSQPEATKC FQWQRNMRKR RRR;

(SEQ ID NO: 4)
RRRRRRSVQW CAVSQPEATK CFQWQRNMRK RRRR;

(SEQ ID NO: 5)
RRRRRRSVQW QAVSQPIATE QFQWQRNMRK RRR;

(SEQ ID NO: 6)
RRRRRRSVQW AAVSQPIATE AFQWQRNMRK RRR;

(SEQ ID NO: 7)
RRRRRRSVQW QAVSQPEATK QFQWQRNMRK RRR;

(SEQ ID NO: 8)
RRRRRRSVQW QAVSQPGATK QFQWQRNMRK RRR;

(SEQ ID NO: 9)
RRRRRRSVQW QAVSQPIATK QFQWQRNMRK RRR;

(SEQ ID NO: 10)
RRRRRRSVQW QAVSQPQATG QFQWQRNMRK RRR;

(SEQ ID NO: 11)
RRRRRRSVQW QAVSQPIATI QFQWQRNMRK RRR;
or
                                   (SEQ ID NO: 12)
RRRRRRSVQW AAVSQPIATK AFQWQRNMRK RRR.
```

The terms "analog", "modification" and "derivative" refer to biologically active derivatives of the reference molecule that retain desired activity as described herein. In general, the term "analog" refers to compounds having a native polypeptide sequence and structure with one or more amino acid additions, substitutions (generally conservative in nature) and/or deletions, relative to the native molecule, so long as the modifications do not destroy activity and which are "substantially homologous" to the reference molecule as defined herein. Preferably, the analog, modification or derivative has at least the same desired activity as the native molecule, although not necessarily at the same level. The terms also encompass purposeful mutations that are made to the reference molecule. Particularly preferred modifications include substitutions that are conservative in nature, i.e., those substitutions that take place within a family of amino acids that are related in their side chains. Specifically, amino acids are generally divided into four families: acidic, basic, non-polar and uncharged polar. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the molecule of interest may include up to about 5-20 conservative or non-conservative amino acid substitutions, so long as the desired function of the molecule remains intact. One of skill in the art can readily determine regions of the molecule of interest that can tolerate change by reference to Hopp/Woods and Kyte Doolittle plots, well known in the art.

By "fragment" is intended a molecule consisting of only a part of the intact full-length polypeptide sequence and structure. The fragment can include a C terminal deletion, an N terminal deletion, and/or an internal deletion of the native polypeptide. A fragment will generally include at least about 5-10 contiguous amino acid residues of the full length molecule, preferably at least about 15-25 contiguous amino acid residues of the full length molecule, and most preferably at least about 20 50 or more contiguous amino acid residues of the full length molecule, or any integer between 5 amino acids and the full length sequence, provided that the fragment in question retains the ability to elicit the desired biological response, although not necessarily at the same level.

The term "derived from" is used to identify the original source of a molecule (e.g., bovine or human) but is not meant to limit the method by which the molecule is made which can be, for example, by chemical synthesis or recombinant means.

As used herein, the term "a therapeutically effective amount" refers an amount sufficient to achieve the intended purpose. For example, an effective amount of lactoferrin will cause generation and expansion of MDSCs as the term is defined herein. An effective amount of MDSCs will inhibit the immune system, including suppression of T cells. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. The effective amount in each individual case may be determined by a skilled artisan according to established methods in the art.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

Routes of administration include, but are not limited to, intradermal, intramuscular, intraperitoneal, intravenous, subcutaneous, intranasal, epidural, and oral routes. The agent may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Myeloid-derived suppressor cells (MDSCs) are pathologically activated and relatively immature myeloid cells that have been implicated in the immunological regulation of many pathologic conditions. Phenotypically and morphologically, MDSCs are similar to neutrophils (polymorphonuclear) (PMN-MDSCs) and monocytes (M-MDSCs). However, they have potent suppressive activity and distinct gene expression profiles and biochemical characteristics. No or very few MDSCs are observed in steady state physiological conditions. Therefore, until recently, accumulation of MDSCs was considered a consequence of pathological processes or pregnancy.

As noted above, MDSCs can be grouped into subsets: PMN-MDSC and M-MDSC, which are phenotypically and morphologically distinct, and also have unique (although partially overlapping) functional characteristics and biochemical traits, which reflect their different roles under various pathological conditions. MDSCs can have multiple phenotypes, including PMN-MDSC) (CD11b$^+$Ly6G$^+$Ly6C$^{lo}$) and M-MDSC (CD11b$^+$Ly6G$^-$Ly6C$^{hi}$). As used herein, the term MDSC refers to all cells having the phenotype, morphology and/or activity of a MDSC. Such criteria include those described by Bronte et al, Recommendations for myeloid-derived suppressor cell nomenclature and characterization standards, Nat Commun. 2016; 7: 12150, which is incorporated herein by reference. Such activity includes the suppression of T cells. Methods to evaluate suppressive activity are known in the art and are further described herein. Other indicia of MDSC activity include the ability to control inflammation, decrease presence of leukocytes, decrease amounts of IgE, decrease amounts of IL-13 and/or decrease amounts of IL-14. Methods are known in the art for assaying these properties.

As used herein, "disease", "disorder" and "condition" are used interchangeably, to indicate an abnormal state in a subject.

As used herein, the term inflammatory condition or inflammatory disease refers to a disorder in which the immune system attacks the body's own cells or tissues, resulting in abnormal inflammation. Inflammation includes or results in chronic pain, redness, swelling, stiffness, and damage to normal tissues. The term inflammatory condition or disease includes autoimmune diseases such as multiple sclerosis, lupus, asthma, autoimmune hepatitis, diabetes, rheumatoid arthritis, psoriasis, inflammatory bowel disease, Addison's disease, Graves' disease, Sjögren's syndrome, Hashimoto's thyroiditis, myasthenia gravis, vasculitis, pernicious anemia, and celiac disease. Other inflammatory conditions include bacterial infections, colitis, osteoarthritis, and allergy. In one embodiment, the inflammatory condition is asthma. In another embodiment, the inflammatory condition is hepatitis. In yet another embodiment, the inflammatory condition is colitis. In one embodiment, the inflammatory condition is necrotizing enterocolitis (NEC). In another embodiment, the inflammatory condition is sepsis. In yet another embodiment, the inflammatory condition is bronchopulmonary dysplasia (BPD).

In one embodiment, the inflammatory condition is necrotizing enterocolitis (NEC). NEC is an idiopathic, inflammatory bowel necrosis of premature infants, which can have devastating effects. The treatment of NEC includes gastrointestinal rest, gastric decompression, broad-spectrum intravenous antibiotics, and systemic support.

Methods of Generating MDSC

In one aspect, provided herein are methods of generating MDSCs ex vivo. The method includes culturing one or more type of blood cell with lactoferrin. The blood cells, sometimes called "source blood", useful herein include white blood cells, or blood fractions containing the same. Useful blood cells/sources also include cord blood cells, peripheral blood mononuclear cells (PMBC), bone marrow cells, whole blood, pluripotent stem cells, induced pluripotent stem cells, and multipotent stem cells. In one embodiment, the blood cells are a cell type or types which is/are isolated from one or more of the cell types/sources described herein. In one embodiment, the blood cells are PBMCs. In another embodiment, the cells are cord blood cells. In another embodiment, the cells are CD14+ cells. In another embodiment, the cells are monocytes. In another embodiment, the cells are granulocytes (or polymorphonuclear neutrophils, PMN). In yet another embodiment, the cells are CD34+ progenitor cells.

The blood cells may, in one embodiment, be derived from the same subject to which they will ultimately be administered (i.e., an autologous transfusion). In another embodiment, the source of the blood cells is a donor or donors.

In one embodiment, the MDSCs may be generated ex vivo. As used herein, ex vivo refers to a procedure in which an organ, cells, or tissue are taken from a living body for treatment or procedure, and then returned to the living body of the same or different subject.

The first step of the MDSC generation process involves isolation of the source blood. In one embodiment, PMN cells are isolated or enriched from the source blood. Techniques for isolating PMN from whole blood or other sources are known in the art. In one embodiment, PMN are isolated using negative selection with magnetic beads (Fan et al, Interrogating Parkinson's disease LRRK2 kinase pathway activity by assessing Rab10 phosphorylation in human neutrophils, Biochem J. 2018 Jan. 15; 475(1): 23-44 (online publication November 2017). In another embodiment, PMN are isolated using a density gradient (Oh et al, Neutrophil Isolation Protocol, J Vis Exp. 2008; (17): 745 (July 2008), Kuhns et al, Isolation and Functional Analysis of Human Neutrophils, Curr Protoc Immunol. November 2015; 111: 7.23.1-7.23.16, both of which are incorporated herein by reference). In one embodiment, PMN are isolated from cord blood (CB) of healthy individuals using negative selection with magnetic beads.

In another embodiment, monocytes (MON) are isolated or enriched. Monocytes can be isolated using techniques known in the art, including isolation of CD14+ cells from PBMC using magnetic beads (Heideveld et al, CD14+ cells from peripheral blood positively regulate hematopoietic stem and progenitor cell survival resulting in increased erythroid yield, Haematologica. 2015 November; 100(11): 1396-1406) and density gradients (Repnik et al, Simple and cost-effective isolation of monocytes from buffy coats, J Immunol Methods. 2003 July; 278(1-2):283-92). Both of these references are incorporated herein.

In another embodiment, CD34+ progenitor cells are isolated or enriched from the source blood. CD34+ progenitors can be isolated using techniques known in the art, including isolation of CD34+ cells from mononuclear cells from human bone marrow, peripheral blood or cord blood using magnetic beads (Mandle et al, Infection of human CD34+ progenitor cells with *Bartonella henselae* results in intraerythrocytic presence of *B. henselae*, Blood. 2005 Aug. 15; 106(4):1215-22. Epub 2005 Apr. 28, which is incorporated herein by reference).

In one embodiment, PMN and/or MON are generated from CD34+ progenitors using techniques known in the art. Such techniques include culture with one or more cytokines. Such cytokines include granulocyte-macrophage colony-stimulating factor (GM-CSF), granulocyte colony-stimulating factor (G-CSF), flt-3 ligand (Flt3-L), stem cell factor (SCF), interleukin 3 (IL-3), interleukin 6 (IL-6), fetal bovine serum (FBS) and thrombopoietin (TPO). Concentrations of cytokines may be established based on culture conditions, but may range from about 5 ng/mL to about 500 ng/mL, including endpoints and all numbers therebetween. Cytokine concentrations may include 5 ng/mL, 10 ng/mL, 15 ng/mL, 20 ng/mL, 25 ng/mL, 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 105 ng/mL, 110 ng/mL, 115 ng/mL, 120 ng/mL, 125 ng/mL, 130 ng/mL, 135 ng/mL, 140 ng/mL, 145 ng/mL, 150 ng/mL, 155 ng/mL, 160 ng/mL, 165 ng/mL, 170 ng/mL, 175 ng/mL, 180 ng/mL, 185 ng/mL, 190 ng/mL, 195 ng/mL, 200 ng/mL, 205 ng/mL, 210 ng/mL, 215 ng/mL, 220 ng/mL, 225 ng/mL, 230 ng/mL, 235 ng/mL, 240 ng/mL, 245 ng/mL, 250 ng/mL, 255 ng/mL, 260 ng/mL, 265 ng/mL, 270 ng/mL, 275 ng/mL, 280 ng/mL, 285 ng/mL, 290 ng/mL, 295 ng/mL, 300 ng/mL, 305 ng/mL, 310 ng/mL, 315 ng/mL, 320 ng/mL, 325 ng/mL, 330 ng/mL, 335 ng/mL, 340 ng/mL, 345 ng/mL, 350 ng/mL, 355 ng/mL, 360 ng/mL, 365 ng/mL, 370 ng/mL, 375 ng/mL, 380 ng/mL, 385 ng/mL, 390 ng/mL, 395 ng/mL, 400 ng/mL, 405 ng/mL, 410 ng/mL, 415 ng/mL, 420 ng/mL, 425 ng/mL, 430 ng/mL, 435 ng/mL, 440 ng/mL, 445 ng/mL, 450 ng/mL, 455 ng/mL, 460 ng/mL, 465 ng/mL, 470 ng/mL, 475 ng/mL, 480 ng/mL, 485 ng/mL, 490 ng/mL, 495 ng/mL, and 500 ng/mL. The relevant concentration for each cytokine used may be determined individually.

The cells are cultured for the desired amount of time. In one embodiment, the cells are cultured for 1 day to 14 days. In another embodiment, the cells are cultured for 2, 3, 4, 5, 6, 7, 8, 9, 10, 11, 12, 13 or 14 days, or any time therebetween.

In one embodiment, PMN and MON are generated from CD34+ cells using 9-day culture with GM-CSF and G-CSF on the monolayer of OP9 feeder cells. See Jie et al, Large-scale ex vivo generation of human neutrophils from cord blood CD34+ cells, PLoS One. July 2017; 12(7): e0180832, which is incorporated herein by reference.

PMN and MON are then cultured with one or more cytokines (as described above) to protect viability, and lactoferrin to generate MDSCs. In one embodiment, the cytokine includes GM-CSF. The lactoferrin may be any lactoferrin compound as described herein, including any analog, modification, derivative or fragment thereof. In one embodiment, the lactoferrin is a lactoferrin related peptide as described in U.S. Pat. No. 7,420,033, which is incorporated herein by reference. In one embodiment, the lactoferrin is that shown in SEQ ID NO: 1. In another embodiment, the lactoferrin is selected from recombinant human lactoferrin, a lactoferrin peptide (33-mer), talactoferrin alfa, VEN-100, VEN-120, VEN-150, hLF-111, PRC-14, PRC14, Lf-HA-DOX, AdeLact, ALX-009, or other lactoferrin described herein or known in the art.

The cells are cultured with lactoferrin in an amount ranging from about 0.01 mg/ml to about 10 mg/ml, including all amounts therebetween and end points. In one embodiment, the LF concentration is about 0.1 mg/ml to about 5 mg/ml, including all amounts therebetween and end points. In another embodiment, the LF concentration is about 0.3 mg/ml to about 1.0 mg/ml, including all amounts therebetween and end points. In another embodiment, the LF concentration is about 0.3 mg/ml. In another embodiment, the LF concentration is about 0.4 mg/ml. In another embodiment, the LF concentration is about 0.5 mg/ml. In another embodiment, the LF concentration is about 0.6 mg/ml. In another embodiment, the LF concentration is about 0.7 mg/ml. In another embodiment, the LF concentration is about 0.8 mg/ml. In another embodiment, the LF concentration is about 0.9 mg/ml. In another embodiment, the LF concentration is about 1.0 mg/ml.

The cells are cultured with lactoferrin for a time sufficient to generate MDSCs. In one embodiment, the cells are cultured with LF for about 1 hour to about 72 hours. In another embodiment, cells are collected for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. In one embodiment, cells are collected after 6, 12, 24, and 48 hrs.

Viability of the cells is assessed via known techniques (e.g., trypan blue staining). In one embodiment, the cells are further tested if viability is above a certain threshold. In one embodiment, viability is above 50%, 55%, 60%, 70%, 75%, 80%, 85%, 90%, or 95%. In a preferred embodiment, if viability is at or above 75%, cells are tested further to determine whether they meet the characterization criteria for MDSC. Such tests include those described by Bronte et al, Recommendations for myeloid-derived suppressor cell nomenclature and characterization standards, Nat Commun. 2016; 7: 12150, which is incorporated herein by reference.

In some embodiments, phenotypic studies are performed. As noted above, MDSC may fall into one of the following subpopulations: PMN-MDSC (CD11b$^+$Ly6G$^+$Ly6C$^{lo}$) and M-MDSC (CD11b$^+$Ly6G$^-$Ly6C$^{hi}$). In human peripheral blood mononuclear cell (PBMC), the equivalent to PMN-MDSC are defined as CD11b$^+$CD14$^-$CD15$^+$ or CD11b$^+$CD14$^-$CD66b$^+$ and M-MDSC as CD11b$^+$CD14$^+$HLA-DR$^{-/lo}$CD15$^-$. CD33 myeloid marker can be used instead of CD11b since very few CD15$^+$ cells are CD11b$^-$. While M-MDSC express the myeloid marker CD33, PMN-MDSC display CD33$^{dim}$ staining. Lin$^-$ (including CD3, CD14, CD15, CD19, CD56) HLA-DR$^-$CD33$^+$ cells contain mixed groups of MDSC comprising more immature progenitors. These cells have been defined as early-stage MDSC (eMDSC).

In some embodiments, the cells are tested in a T cell suppression assay to assess MDSC suppressive activity. Such assays are known in the art, and are described herein. In brief, sorted CD3+ T cells from the spleen are labeled with CFSE, stimulated with anti-CD3-coated plates and soluble anti-CD28, and cultured alone or with M-MDSCs at different ratios for 3 d. Cells are then stained with anti-CD4-PE-Cy5 and anti-CD8a-PE, and T-cell proliferation is analyzed by flow cytometry. See, He et al, Nat Med. 2018 February; 24(2):224-231.doi: 10.1038/nm.4467. Epub 2018 Jan. 15, which is incorporated herein by reference in its entirety.

Other methods of assessing MDSC activity include inhibition of 3H-thymidine incorporation or CFSE dilution; inhibition of cytotoxic T lymphocyte activity; inhibition of IFN-γ production by T cells in ELISPOT or intracellular staining; inhibition of expression of CD3 chain on T cells; inhibition of IL-2 production; inhibition of anti-CD3/CD28 (or PHA) induced T-cell proliferation or IFN-γ production (in ELISPOT or by intracellular staining) by the addition of candidate MDSC populations; and improved T-cell proliferation after removal of candidate MDSC populations. See Bronte et al, cited above.

In another embodiment, the cells are tested to see if they induce anti-bacterial activity by evaluating phagocytosis and cytotoxicity against *E. coli* and *C. albicans*. Assays to evaluate phagocytosis and cytotoxicity against bacteria. See, e.g., Hofman et al, Increased *Escherichia coli* Phagocytosis in Neutrophils That Have Transmigrated across a Cultured Intestinal Epithelium, Infect Immun. 2000 February; 68(2): 449-455 and Li et al, A critical concentration of neutrophils is required for effective bacterial killing in suspension, PNAS Jun. 11, 2002 99 (12) 8289-8294, which are incorporated herein by reference.

In another embodiment, the cells are subjected to an allogeneic mixed leukocyte reaction (MLR) to assess functional activity. In one embodiment, a three-way allogeneic MLR is performed. This assay utilizes cells obtained from a pair of unrelated healthy donors: one is the source of T cells, the other one provides APCs. The pair is selected based on strong T-cell proliferative or IFN-γ responses of the responder, and aliquots of cells can be stored for use in subsequent iterative experiments. MDSCs from cancer patients are tested in MLR at different ratios compared with responder T cells. The assay is based on the premise that allogeneic MLR requires presentation of epitopes in the context of MHC class II and class I, so that suppression of responses reflects the ability of MDSC to prevent antigen-specific T-cell immune responses. In one embodiment, as a control, cells are incubated without LF.

In another aspect, the methods provided herein include generating MDSCs in vivo. The method includes administering lactoferrin to a subject in need thereof.

Pharmaceutical Compositions and Administration

In one aspect, provided are pharmaceutical compositions which include MDSC generated according to the methods described herein for treatment of an inflammatory condition or disease. Such pharmaceutical compositions may include pharmaceutically acceptable carriers.

The pharmaceutical compositions and MDSCs described herein are useful in cell therapies, both autologous and allogeneic. Autologous cell therapy (ACT) is a therapeutic intervention that uses an individual's cells, which are cultured and expanded outside the body, and reintroduced into the donor. Advantages of such an approach include the minimization of risks from systemic immunological reactions, bio-incompatibility, and disease transmission associated with grafts or cells not cultivated from the individual. Thus, in one embodiment, the methods include removal of the source blood cells from the donor.

In one aspect, a method of treating an inflammatory disease in a subject is provided. In one embodiment, the method includes administering a therapeutically effective amount of a pharmaceutical composition comprising MDSCs as generated herein. In one embodiment, the therapeutically effective amount is about $1\times10^5$ to about $1\times10^{14}$ cells, preferably $1\times10^8$ to $1\times10^{11}$ cells, including endpoints and all integers therebetween. In another embodiment, the effective amount is about $5\times10^8$ to $2\times10^{10}$ cells, including endpoints and all integers therebetween.

In another aspect, a method of reducing the likelihood of occurrence or severity of an inflammatory disease in a subject is provided. In one embodiment, the method includes administering a therapeutically effective amount of a pharmaceutical composition comprising MDSCs as generated herein.

In one embodiment of these methods, the subject is a child. In another embodiment, the subject is a neonate. In another embodiment, the subject is a neonate having or at risk for necrotizing enterocolitis.

In one aspect, a therapeutically effective amount of MDSCs as generated according to a method described herein, are provided for use in treating an inflammatory disease in a subject.

In another aspect, a method of reducing the likelihood of occurrence or severity of an inflammatory disease in a subject is provided. The method includes administering a therapeutically effective amount of a lactoferrin composition to a subject in need thereof.

In one aspect, provided are pharmaceutical compositions which include lactoferrin compounds as described herein, for treatment of an inflammatory condition or disease and/or for generation or expansion of MDSCs in vivo. Such pharmaceutical compositions may include pharmaceutically acceptable carriers.

The subject of these methods includes any described herein, or for which the health care provided deems the treatment necessary or acceptable. In one embodiment of these methods, the subject is a child. In another embodiment, the subject is a neonate. In another embodiment, the subject is a neonate having or at risk for necrotizing enterocolitis.

In one aspect, a therapeutically effective amount of a lactoferrin composition is provided to the subject in need thereof. As is well known in the art, a specific dose level of active compounds such as the lactoferrin composition or MDSCs for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, and general safety and purity standards as required by FDA Office of Biologics standards.

A therapeutically effective amount of a lactoferrin composition as a treatment varies depending upon the host treated and the particular mode of administration. In one embodiment of the invention the dose range of a peptide composition will be about 0.5 mg/kg body weight to about 500 mg/kg body weight. However, those of skill will recognize the utility of a variety of dosage range, for example, 0.1 µg/kg body weight to 1 µg/kg body weight, 1 µg/kg to 1 mg/kg body weight, 1 mg/kg body weight to 450 mg/kg body weight, 2 mg/kg body weight to 400 mg/kg body weight, 3 mg/kg body weight to 350 mg/kg body weight, 4 mg/kg body weight to 300 mg/kg body weight, 5 mg/kg body weight to 250 mg/kg body weight, 6 mg/kg body weight to 200 mg/kg body weight, 7 mg/kg body weight to 150 mg/kg body weight, 8 mg/kg body weight to 100 mg/kg body weight, or 9 mg/kg body weight to 50 mg/kg body weight. Further, those of skill will recognize that a variety of different dosage levels will be of use, for example, 0.1 µg/kg, 1 µg/kg, 10 µg/kg, 100 µg/kg, 200 µg/kg; 300 µg/kg; 400 µg/kg, 500 µg/kg, 600 µg/kg, 700 µg/kg, 800 µg/kg, 900 µg/kg, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for the compositions of the present invention.

The treatments may include various "unit doses." Unit dose is defined as containing a predetermined quantity of the therapeutic composition (lactoferrin composition) calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

In certain embodiments, the composition is given in a single dose or multiple doses. The single dose may be administered daily, or multiple times a day, or multiple times a week, or monthly or multiple times a month. In a further embodiment, the composition is given in a series of doses. The series of doses may be administered daily, or multiple times a day, weekly, or multiple times a week, or monthly, or multiple times a month.

Dosages and administration regimen can be adjusted depending on the age, sex, physical condition of administered as well as the benefit of the conjugate and side effects in the patient or mammalian subject to be treated and the judgment of the physician, as is appreciated by those skilled in the art. The amount may vary from about 0.1 µg to about 100 g of the lactoferrin composition. In one embodiment, the lactoferrin composition is orally administered in the range of 1 mg to 100 g per day, more preferably about 20 mg to about 10 g per day with the most preferred dose being 4.5 g per day. Intravenously administered lactoferrin can be in the range of 0.1 µg to about to 10 g per day, more preferably about 0.1 g to about 1 mg with the most preferred dose being 250 mg per day. In one embodiment, a composition is intratumorally administered in the range of 0.1 µg to 10 g per day with the most preferred dose being 100 µg per day. Topically, the amount of lactoferrin may vary from about 1 µg to about 100 g. In one embodiment, the topical gel, solution, capsule or tablet comprises a concentration of about 0.01% to about 20% of lactoferrin. More preferably, the topical gel, solution, capsule or tablet may comprise a concentration of about 1% to about 8.5% lactoferrin.

In certain embodiments, it may be desirable to combine the lactoferrin composition of the present invention with other agents effective in the treatment of inflammatory disorders, or with surgery or other medical intervention. Agents "effective in the treatment of inflammatory disorders" are capable of negatively affecting inflammatory conditions in a subject. Anti-inflammatory agents include non-steroidal anti-inflammatory drugs (NSAIDs such as aspirin, ibuprofen, or naproxen); corticosteroids (such as budesonide, hydrocortisone, methylprednisolone, or prednisone); antimalarial medications (such as hydroxychloroquine); disease-modifying antirheumatic drugs, including methotrexate, sulfasalazine, leflunomide, azathioprine, and cyclophosphamide; and biologic drugs such as infliximab, etanercept, adalimumab, certolizumab, golimumab, abatacept, tocilizumab, and rituximab. Other useful drugs include aminosalicylates (or "5-ASAs") that tame inflammation in the gut. These include balsalazide (Colazal), mesalamine (Asacol HD, Delzicol), olsalazine (Dipentum), and sulfasalazine (Azulfidine). Other useful drugs include immunemodulators including azathioprine (Azasan, Imuran) and mercaptopurine (Purinethol, Purixan), and cyclosporine (Gengraf, Neoral, and Sandimmune). In the case of NEC, medical treatment typically consists of bowel rest and decompression, antibacterial therapy, and management of other haematological or electrolyte imbalances. Increased respiratory and cardiovascular support is sometimes needed. In neonates who do not respond adequately to medical management, or if pneumoperitoneum is present, surgical intervention may occur with either use of a peritoneal drain or laparotomy.

In the case where lactoferrin and one or more other agents are provided, such compositions may be administered separately or at the same time. This may be achieved by administering a single composition or pharmacological formulation that includes both agents, or by administering two distinct compositions or formulations, at the same time, or at times close enough so as to result in an overlap of this effect, wherein one composition includes the peptide composition and the other includes the second agent(s).

Alternatively, the lactoferrin may precede or follow the other anti-inflammatory agent or treatment by intervals ranging from minutes to weeks. In embodiments where the compositions are administered or applied separately, one would generally ensure that a significant period of time did not expire between the time of each delivery, such that each composition would still be able to exert an advantageously combined effect on the subject. In such instances, it is contemplated that one may administer both modalities within about 1-14 days of each other and, more preferably, within about 12-24 hours of each other. In some situations, it may be desirable to extend the time period for treatment significantly, however, where several days (2, 3, 4, 5, 6 or 7) to several weeks (2, 3, 4, 5, 6, 7 or 8) lapse between the respective administrations.

The lactoferrin compositions may be administered either prior to, or after, onset of the inflammatory condition. In one embodiment, the lactoferrin composition is administered to neonates at risk for developing one or more condition which would benefit from the treatment described herein, such as NEC, BPD or sepsis. In another embodiment, the subject has already been demonstrating symptoms of the inflammatory disease or condition.

Dosages and administration regimen can be adjusted depending on the age, sex, physical condition of administered as well as the benefit of the conjugate and side effects in the patient or mammalian subject to be treated and the judgment of the physician, as is appreciated by those skilled in the art.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

Over one quarter of extremely preterm infants die during the first months of life. Dysregulation of inflammation and aberrant host-microbial interactions play a central role in the development of the three most common contributors to neonatal mortality: bronchopulmonary dysplasia (BPD), necrotizing enterocolitis (NEC), and sepsis. In recent years, a novel paradigm has emerged that identifies the important role of myeloid-derived suppressor cells (MDSC) in the regulation of newborn inflammation.

We hypothesize that transitory expansion of MDSC may be one of the mechanisms that provides protection against infectious mucosal injury in newborns. We found that MDSC observed in newborn mice have much higher anti-bacterial and anti-fungal activity than neutrophils and monocytes in adults. This may provide a crucial, additional layer of protection in newborns. Our data indicate that the appearance of MDSC is closely connected to gestational maturity, with significantly lower expression observed in very premature babies who are at high risk for BPD, NEC, and sepsis. The overall goal of this study is to determine the mechanism and clinical significance of MDSC accumulation in preterm newborns and characterize the therapeutic potential of these cells in the prevention and recovery from BPD, NEC, and sepsis.

Figure 3A:
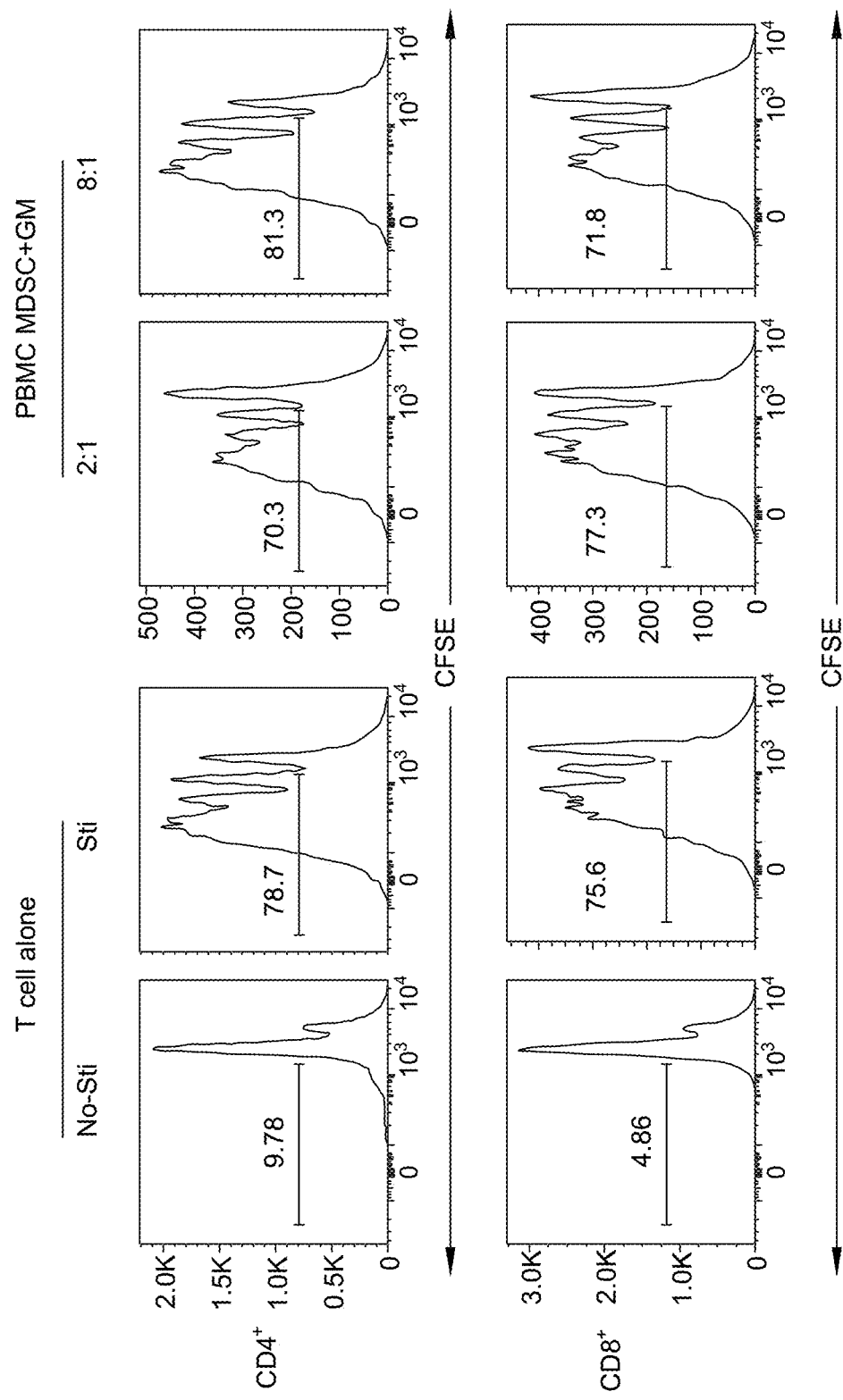
FIG. 3. Suppression activity of LF treated PMN-MDSC. Human cord blood cells were cultured with LF for 1 (FIG. 3A) or 2 days (FIG. 3B) as in FIG. 1. CD15+ PMN-MDSC were isolated and used for suppression of CD3/CD28 activated CD4+ or CD8+ T cells. Top-panels—example of staining. Bottom panel—cumulative results of three experiments.
Figure 3B:
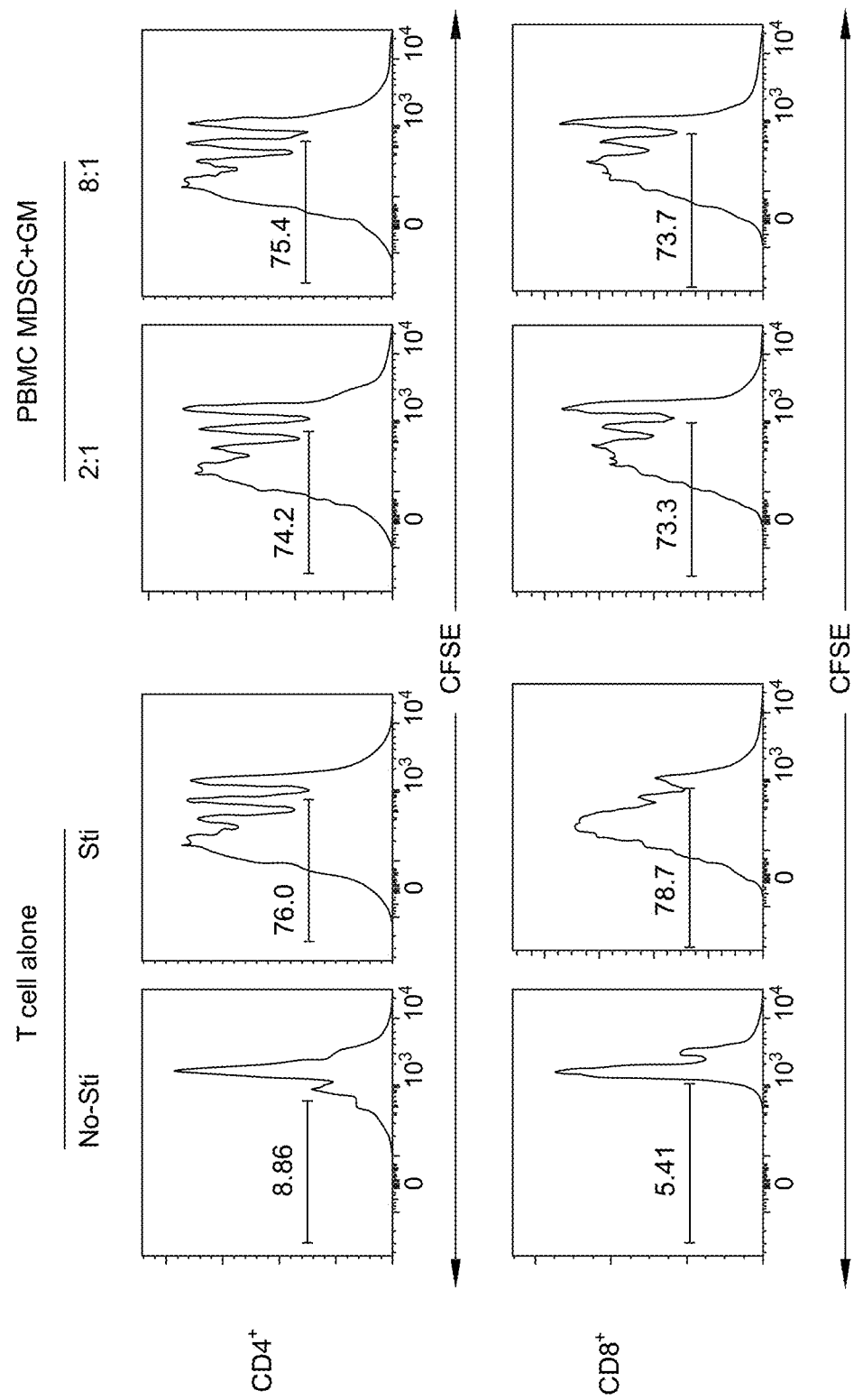

Example 1: Lactoferrin (LF) is Involved in Acquisition of Suppressive Activity by PMN and MON What could drive expansion of MDSC in NBM? The inventors have demonstrated that expansion of MDSC was not the result of the transfer from mothers or caused by normal bacterial colonization in NBM49. It was hypothesized that accumulation of MDSC in NBM could be linked with the consumption of breastmilk. It is known that LF, a component of milk has potent immunoregulatory activity 50. NBM had higher plasma level of LF than adult mice (FIG. 3a). The effect of LF on myeloid cells was tested in vivo by treating 3-week old mice (that lack MDSC) for 8 days with daily i.p. administration of LF. LF treatment caused accumulation of immune suppressive M-MDSC and PMN-MDSC (FIG. 3b,c). Remarkably, treatment of 6-week old mice with LF did not induce suppressive activity of MDSC. Although it is possible that natural fluctuation of LF content in breastmilk over time 51 could contribute to this phenomenon, it was more likely that myeloid progenitors have different susceptibility to LF at different ages. Treatment of mice with LF recapitulated immune suppressive mechanisms observed in NBM49. To better elucidate the role of LF in MDSC accumulation, evaluated cells were evaluated in NBM with deletion of ltf gene (LF-KO mice). Lack of LF did not cancel the expansion of cells with the phenotype of PMN-MDSC or M-MDSC in NBM. However, in the absence of LF, PMN had no suppressive activity (FIG. 3d). PMN from LF-KO NBM had significantly lower amount of S100A9 and PGE2 than PMN-MDSC from WT NBM49. Taken together, these data indicate that LF may be one of the major factors causing acquisition of immune suppressive activity by MDSC in NBM.

Since myeloid cells can produce LF, it raises the question about the source of LF that drives accumulation of MDSC in NBM. To address this question, WT NBM were cross-fostered with LF KO surrogates and LF KO NBM with WT surrogates. Cross-fostering of WT NBM mice with LF KO dames did not result in generation of immune suppressive PMN-MDSC. In contrast, cross-fostering of LF KO NBM with WT mice generated suppressive PMN-MDSC49. These results indicated that LF in the milk plays a critical role in the generation of MDSC.

Example 2: MDSC Regulates NEC in Mice

Figure 4A:
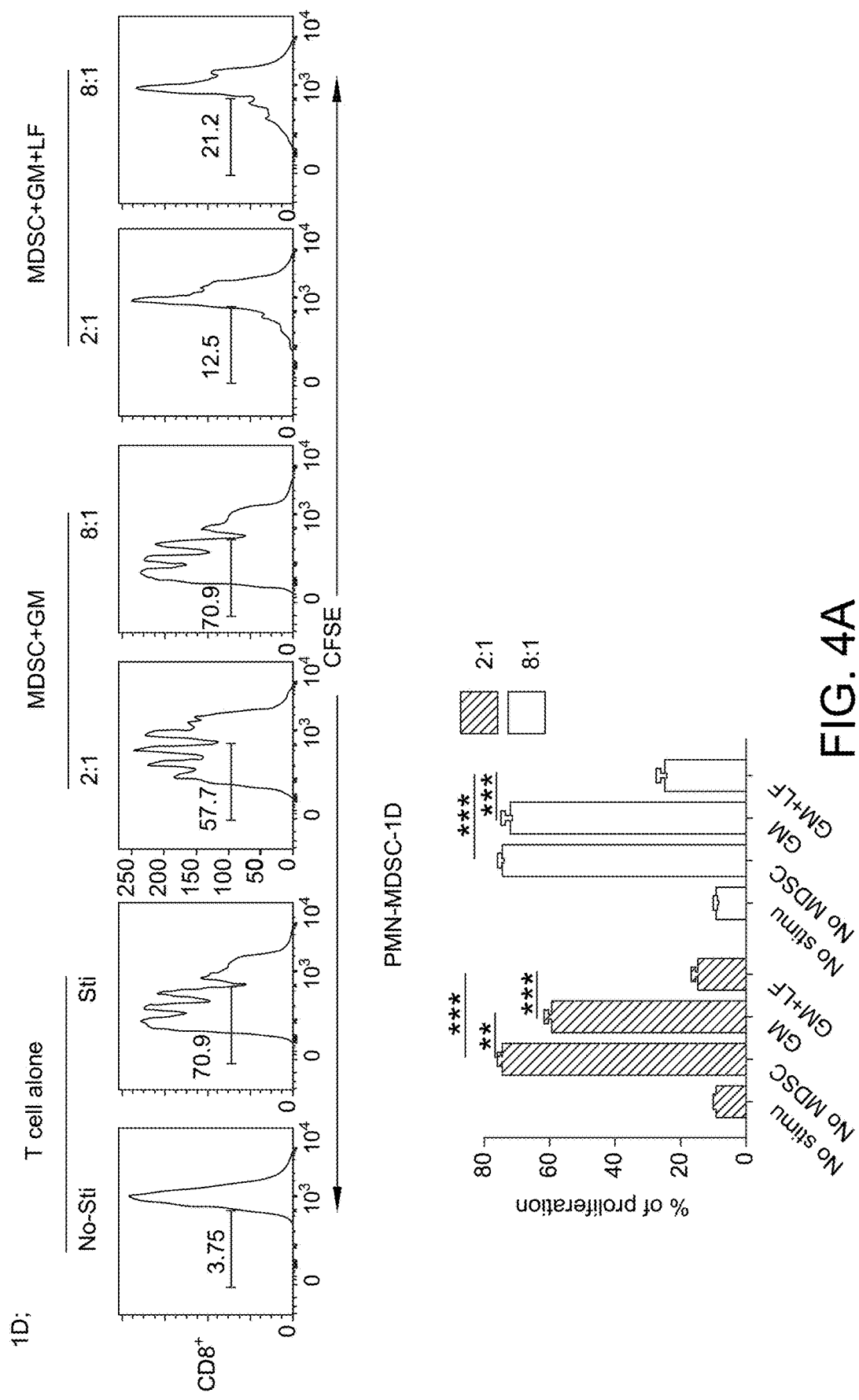
FIG. 4. Experimental conditions of FIG. 3 were replicated with mouse MDSC.
Figure 4B:
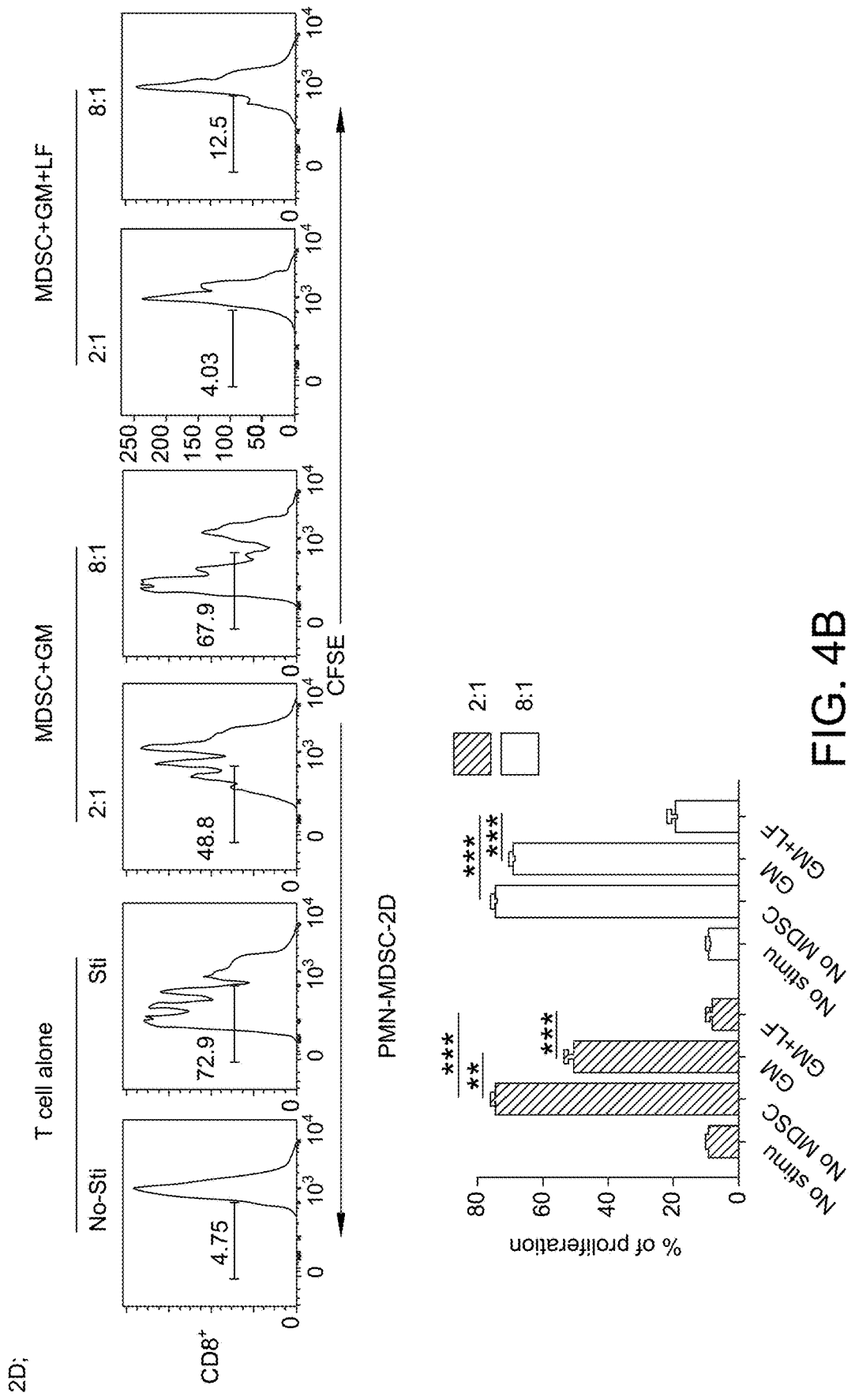
Figure 5A:
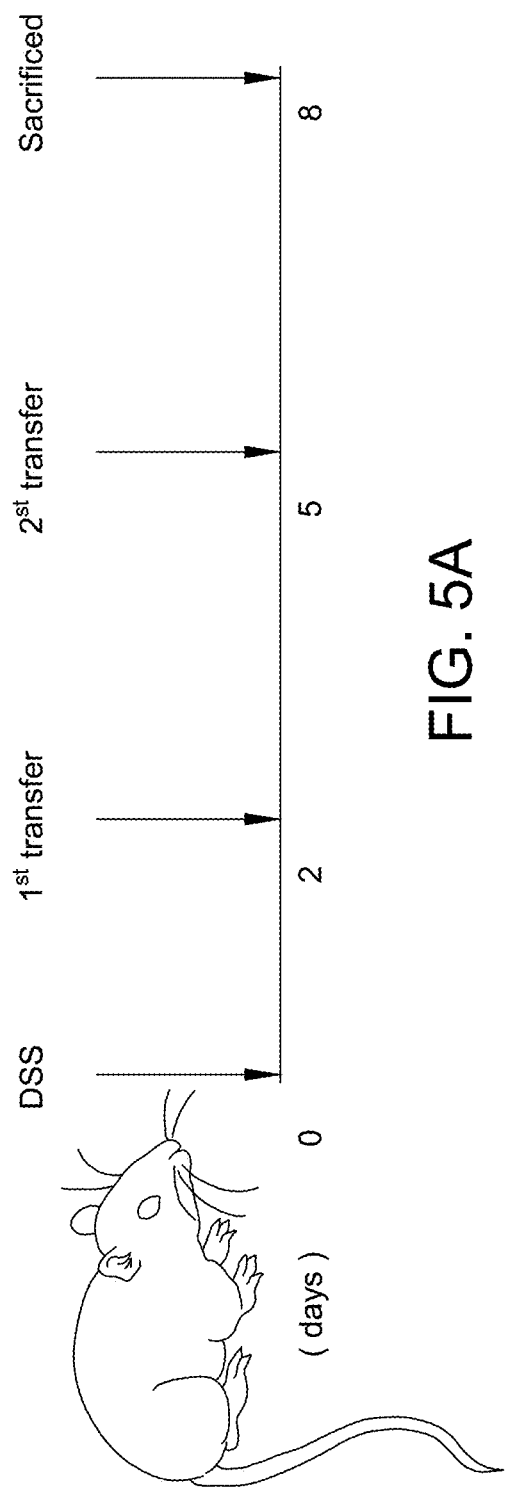
FIG. 5A-FIG. 5F demonstrate that LTF-derived MDSCs attenuates DSS-induced acute colitis.
Figure 5B:
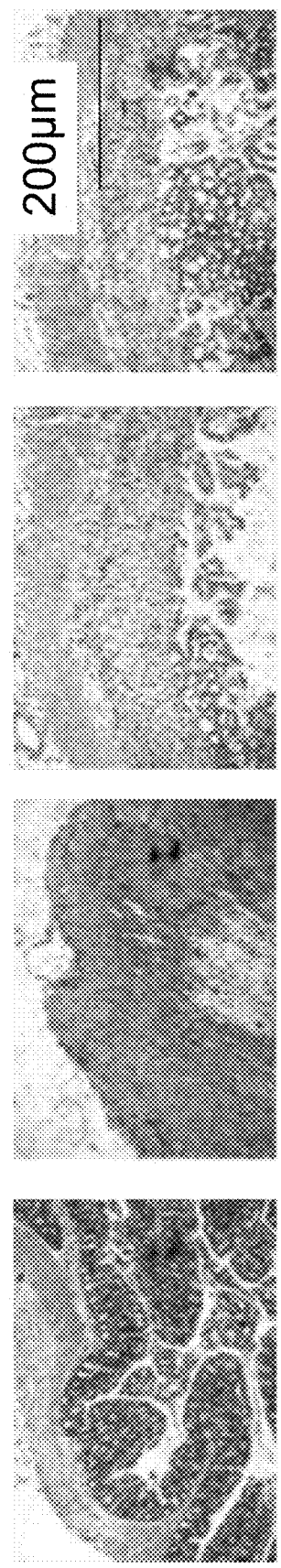
Figure 5C:
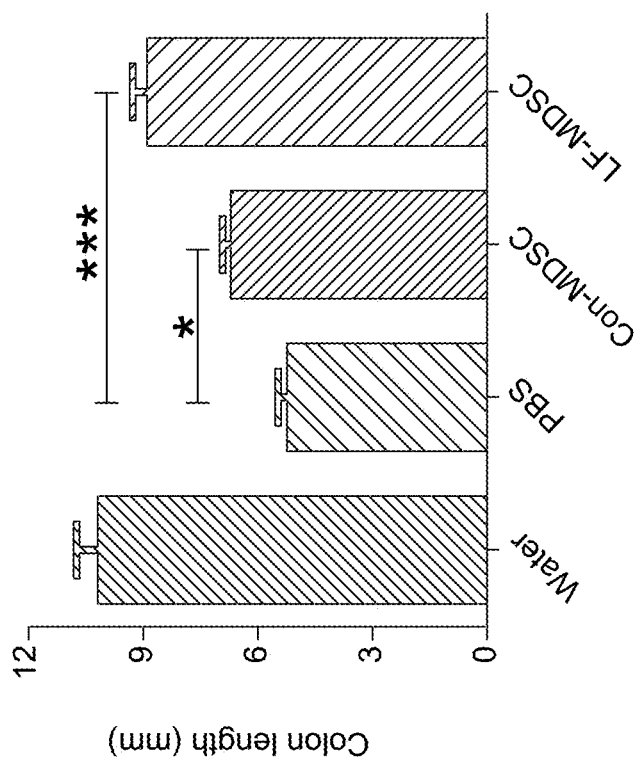
Figure 5C:
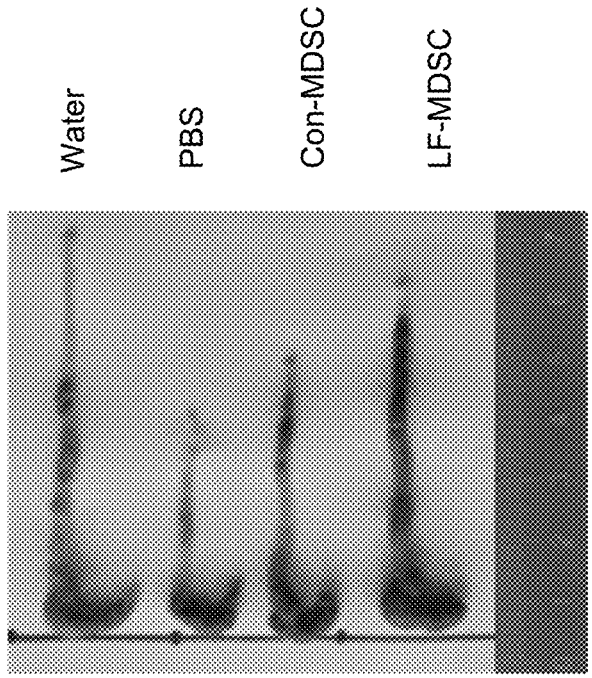
Figure 5D:
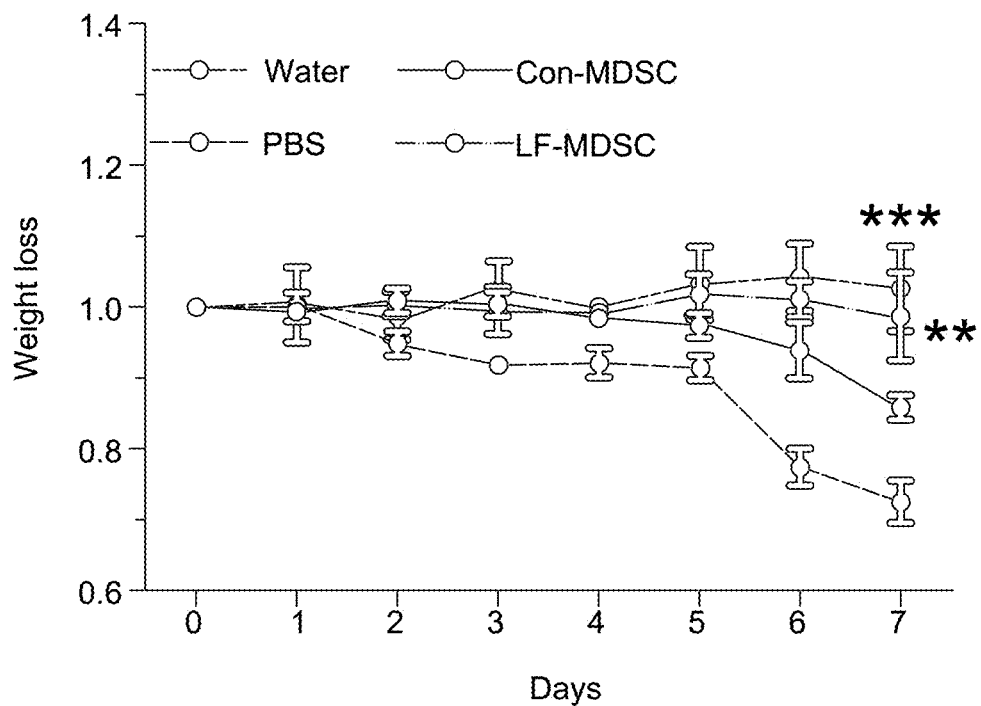
Figure 5E:
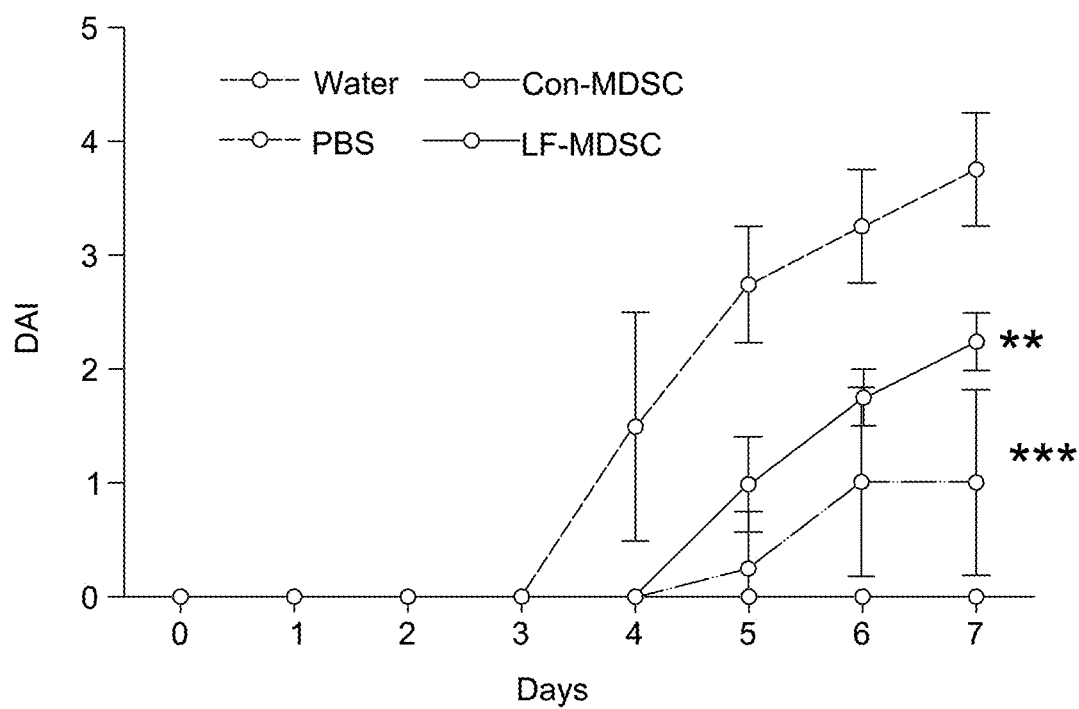
Figure 5F:
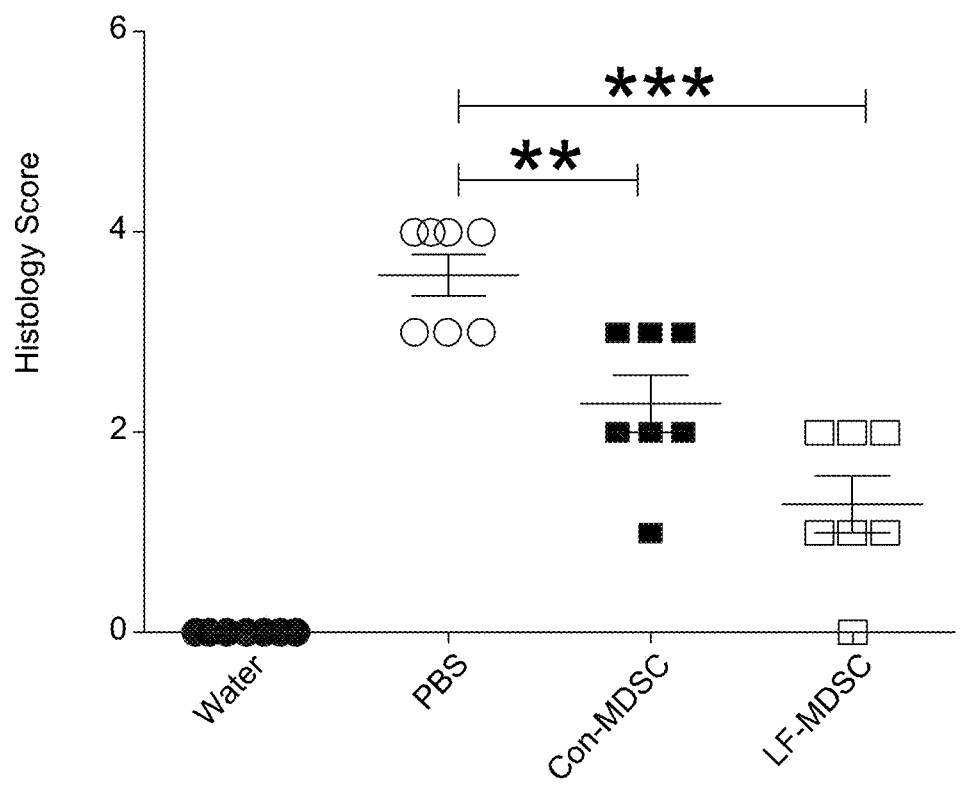
Figure 6A:
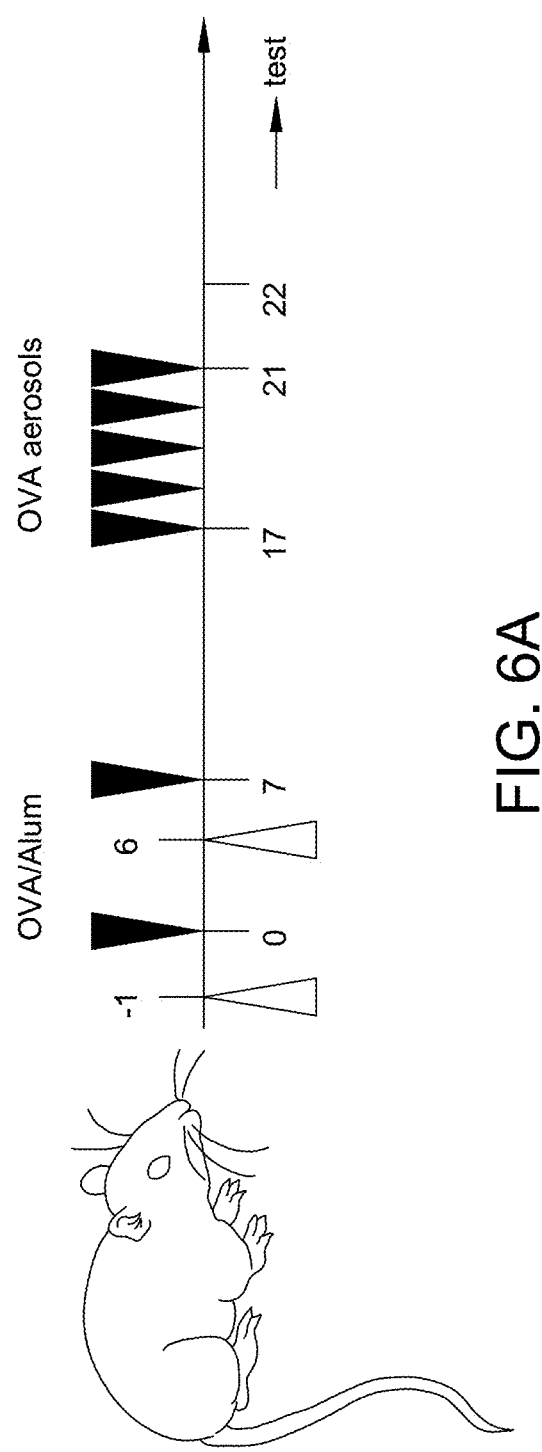
FIG. 6A-FIG. 6E demonstrate that LTF-derived MDSCs attenuates OVA induced asthma.
Figure 6B:
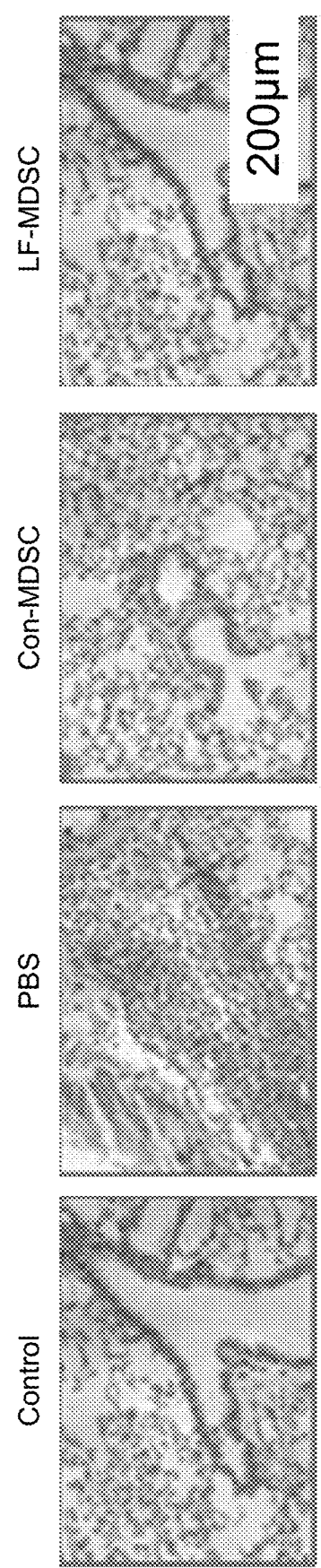
Figure 6C:
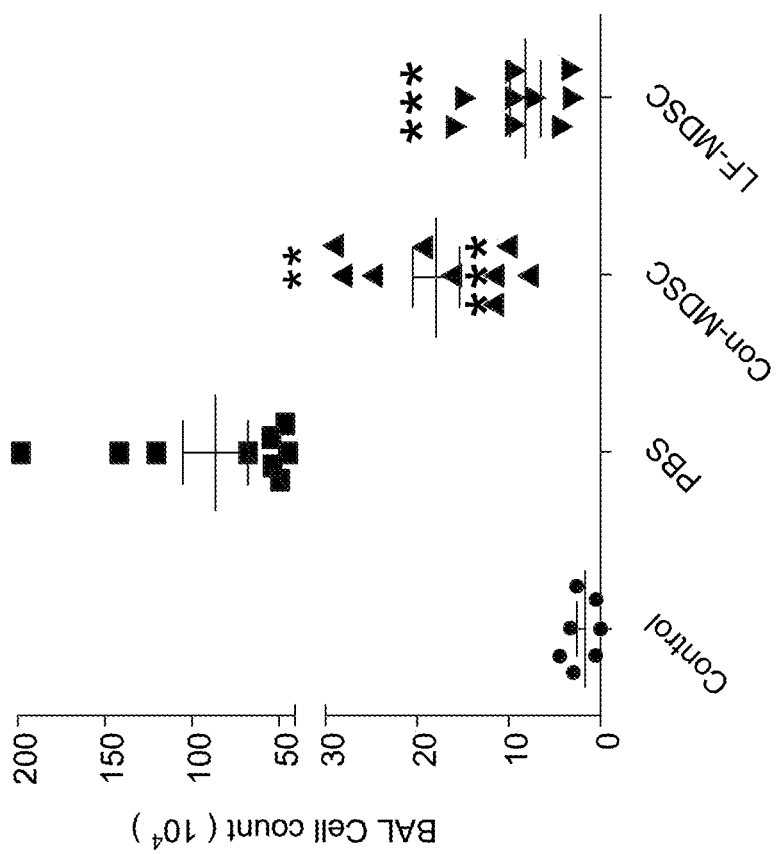
Figure 6C:
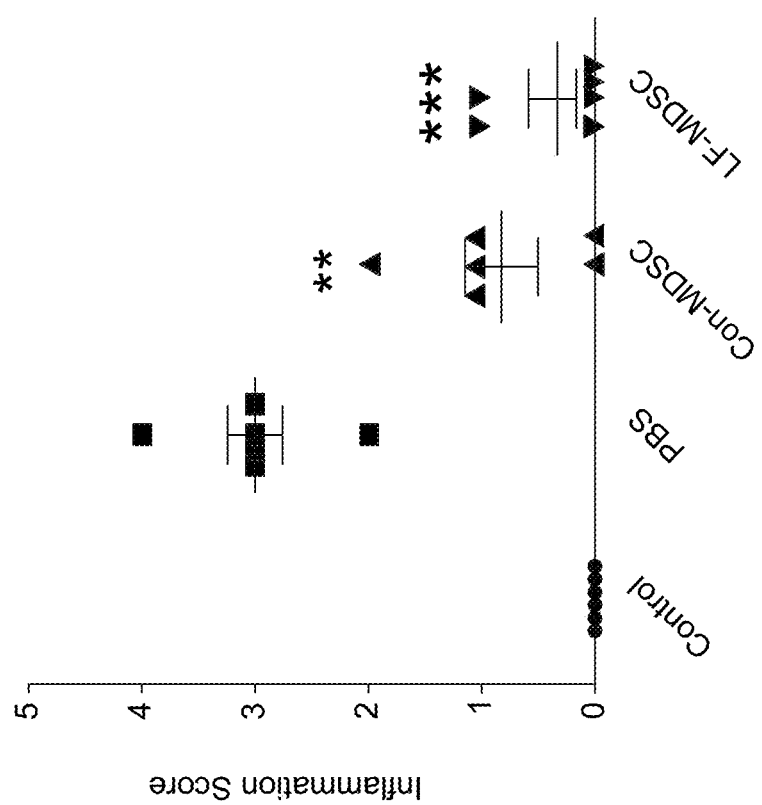
Figure 6D:
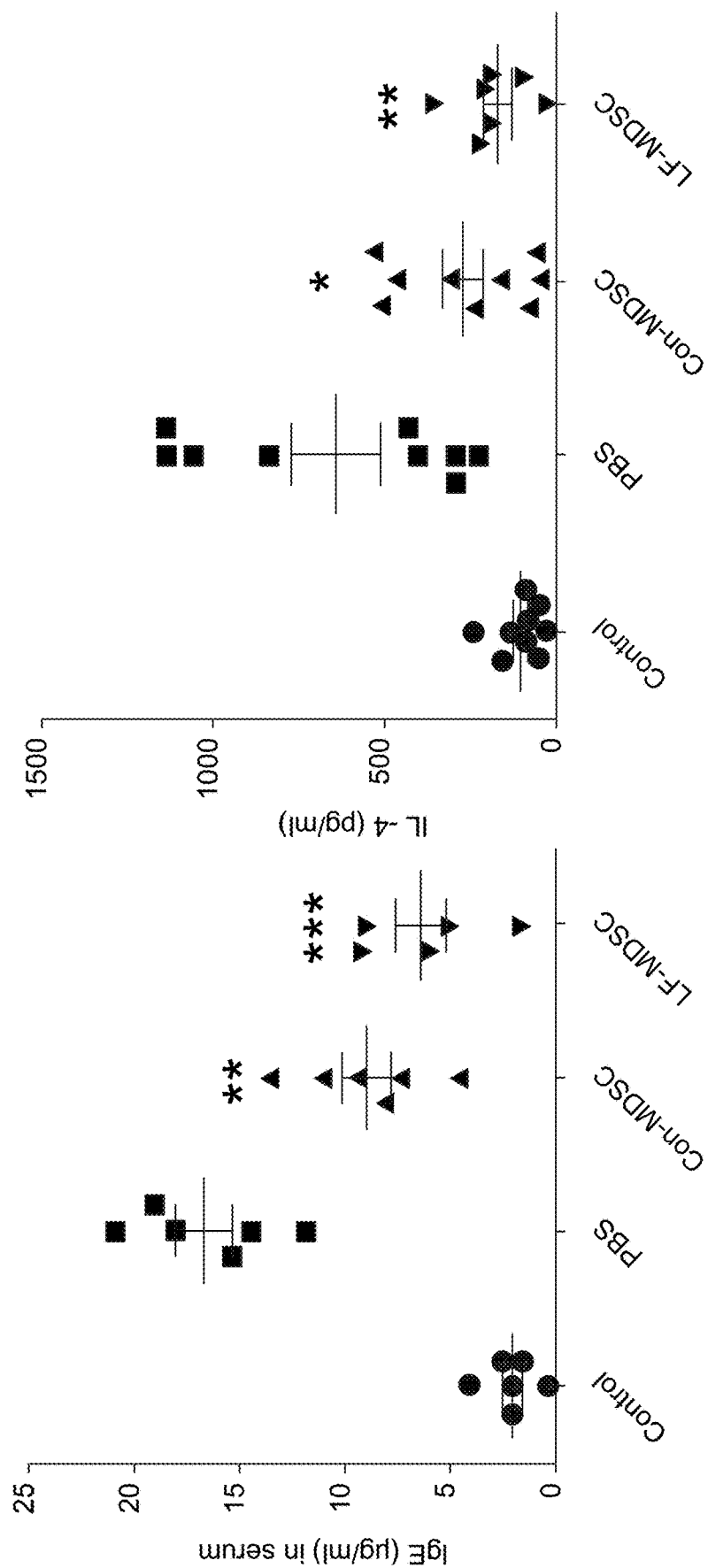
Figure 6E:
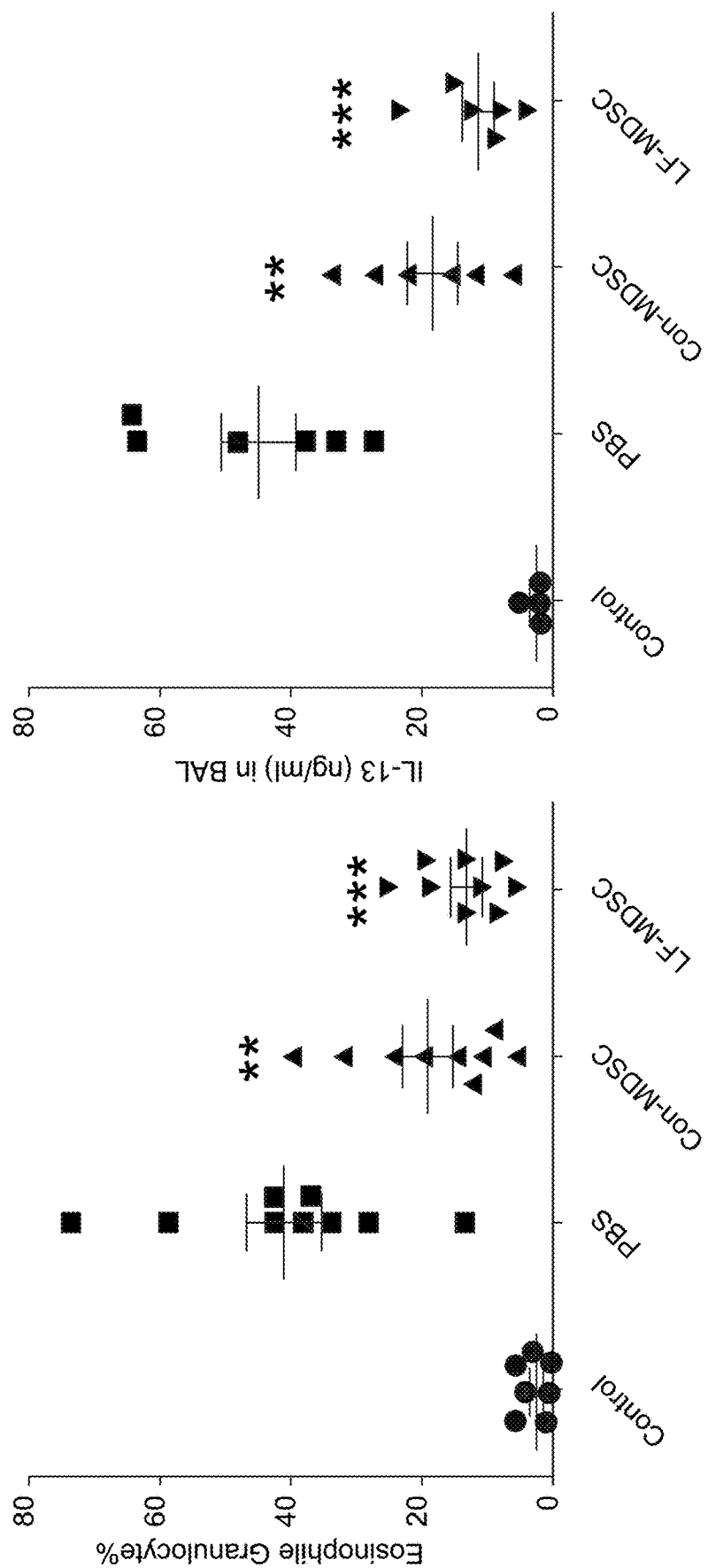
Figure 7A:
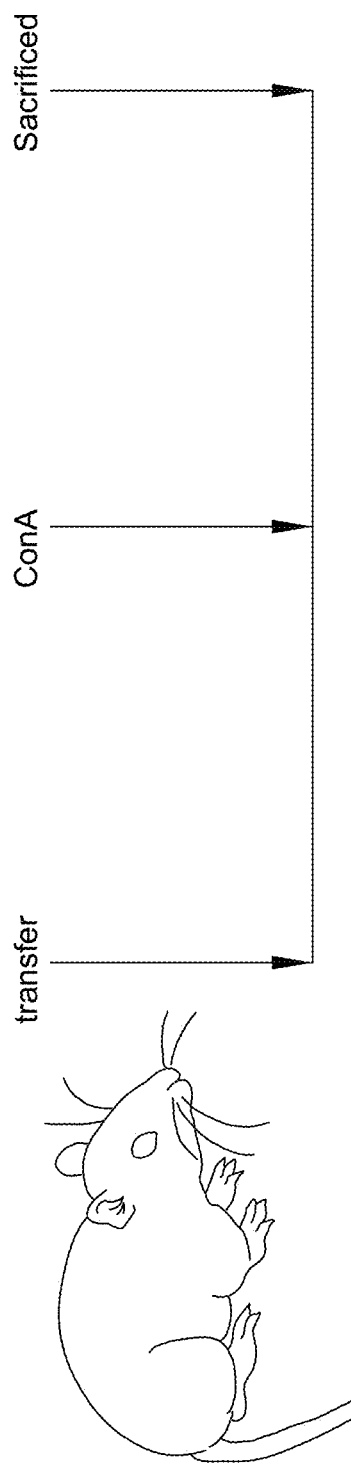
Figure 7B:
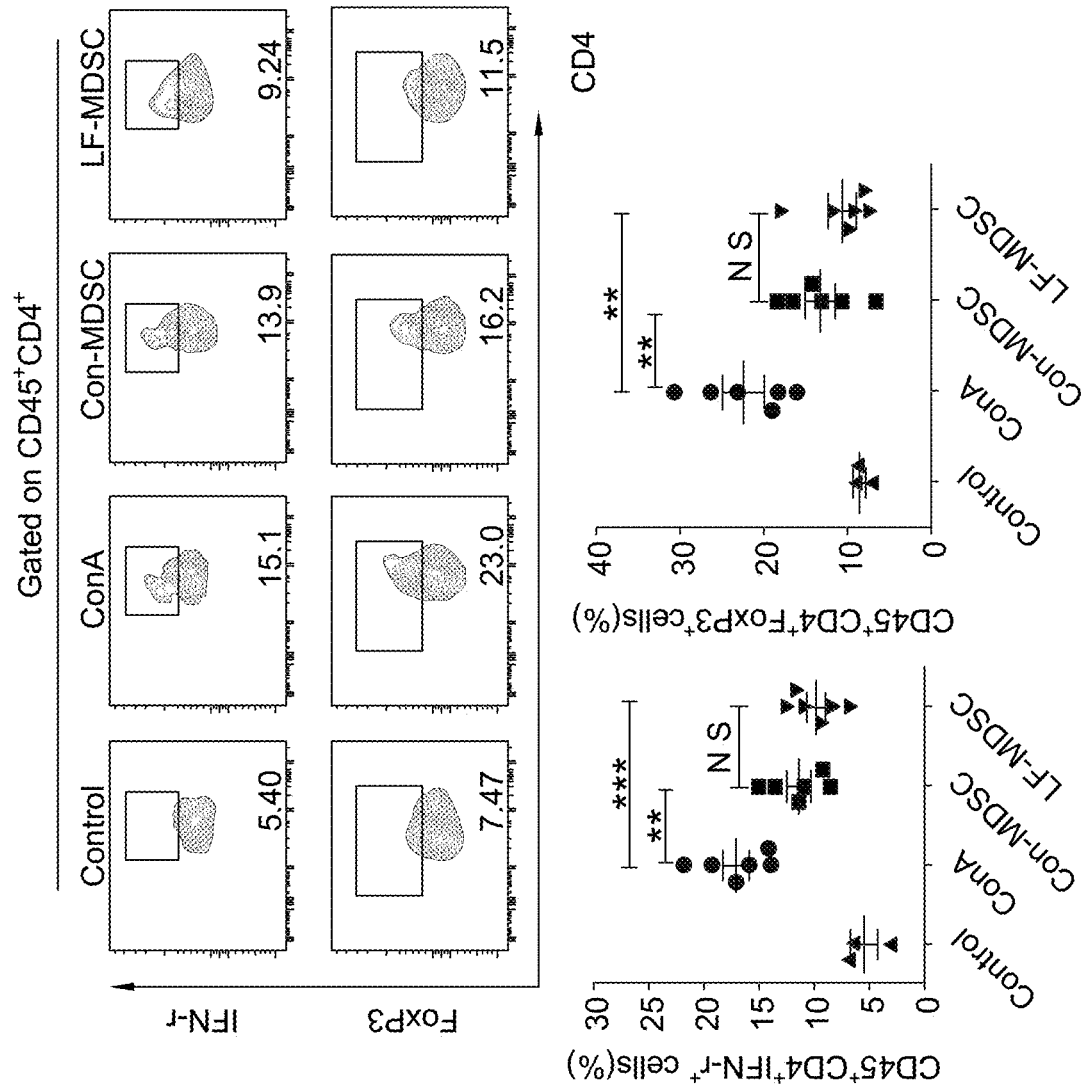
Figure 7E:
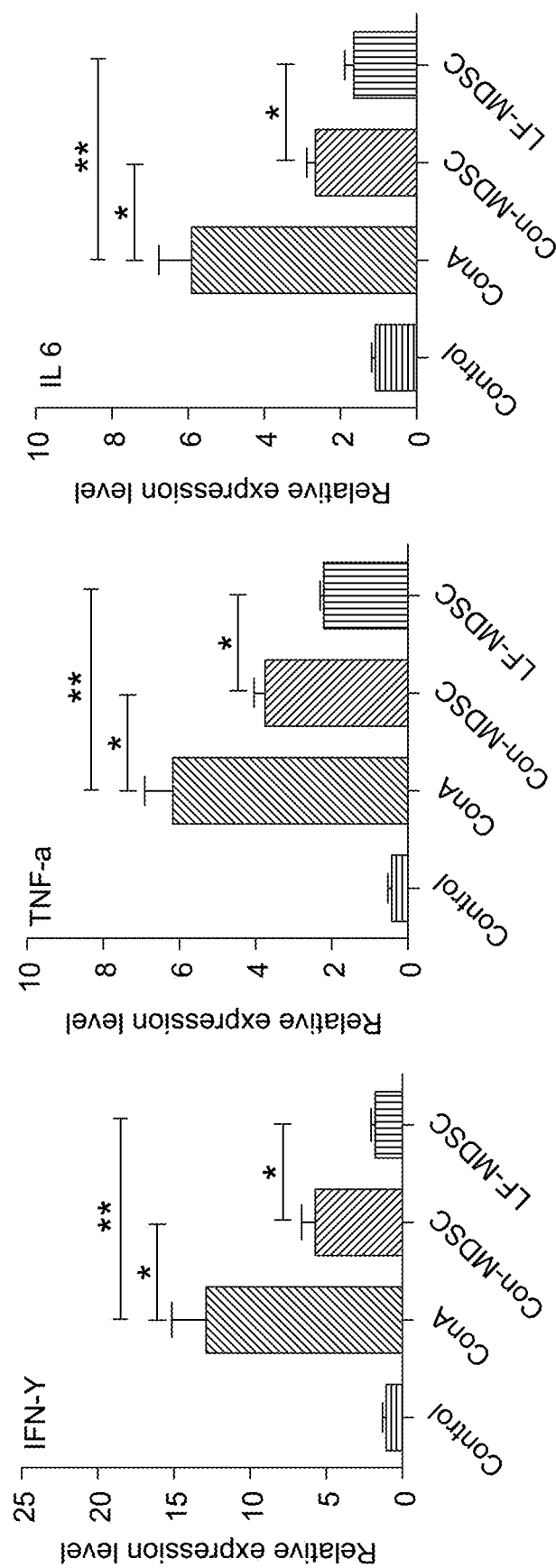

A gavage/hypoxia experimental model of NEC13 was used, which manifests as inflammatory gut injury. Although this model, as with all models of NEC, does not fully recapitulate human disease, it generates conditions (intestinal necrosis and inflammation) that are similar to those observed in humans and is an accepted research surrogate. MDSC in NBM mice were selectively depleted by using agonistic TRAIL-R (DR5) antibody 52-54. NEC was then initiated in 6-day old mice. Injection of DR5 antibodies one day prior to NEC induction resulted in a two-fold decrease in the population of MDSC in the lamina propria (LPMC). This significantly worsened NEC as manifested by shortened survival (FIG. 5a), increased inflammation scores (FIG. 4b), and greater intestine permeability (FIG. 4c). MDSC depletion caused small but significant increases in bacterial load in the intestine (FIG. 4d) and blood49. The effect of MDSC transfer from NBM on NEC development was tested. NBM were treated with PBS or spleen Gr-1+ cells from adult mice (AM) or NBM. After transfer to mice with NEC, MDSC were readily detectable in the intestine49. MDSC from NBM caused a significant decrease in inflammation scores (FIG. 4e) and intestinal permeability (FIG. 40. Gr-1+ cells from AM did not have an effect on gut inflammation (FIG. 4e,f).

Injection of AM cells did not affect survival of mice with NEC. In contrast, MDSC from NBM significantly prolonged survival (FIG. 4g). Transfer of MDSC from NBM decreased bacterial load in both the intestine and circulation. However, there were no differences between the effect of MDSC and cells from AM on bacterial load 49. Consistent with previous report 55, NEC in Rag1 KO mice had significantly lower inflammation and longer survival than WT mice 49. This system was used to dissect the role of MDSC in NEC.

In striking contrast to the effect in WT mice, depletion of MDSC in Rag1KO mice did not affect inflammation scores or survival of the mice 49. Depletion of MDSC did not affect bacterial load in the intestine or circulation in Rag1KO mice. Induction of NEC was associated with up-regulation of Th17 cells as was evidenced by increased presence of IL-17A+ CD4+ T cells and Rorγt+ CD4+ T cells. Administration of myeloid cells from AM did not affect that frequency, whereas MDSC from NBM significantly reduced it. MDSC but not AM cells increased frequency of Tregs 49. These results were consistent with the recent report of positive effect of LF supplementation on the severity of NEC.

Example 3: Evaluation of LF Effect on Suppressive Activity of Human MDSC In Vitro Currently, there is no established method to generate MDSC in humans without using tumor conditioned medium. Two approaches are used to generate MDSC in vitro. First, PMN are isolated from cord blood (CB) of healthy individuals using negative selection with magnetic beads (Miltenyi) and MON after isolating CD14+ cells from PBMC using magnetic beads. Cells are cultured with GM-CSF (5 ng/ml) to protect viability and different concentrations of LF (0.3-1.0 mg/ml). Cells are collected after 6, 12, 24, and 48 hrs, viability is assessed and if above 75%, cells are used in suppression assays. Three-way allogeneic MLR are used, where DCs generated from one donor are mixed with T cells from other donors and MDSC are added at different ratios. This method enables accurate assessment suppressive activity by MDSC92. T-cell proliferation and IFN-γ production is evaluated. As a control, cells are incubated without LF.

In the second procedure, PMN and MON are generated from CD34+ progenitors using 9-day culture with GM-CSF and G-CSF on the monolayer of OP9 feeder cells. PMN and MON are collected and then treated with LF as described above and functional activity is assessed. LF treatment induces anti-bacterial activity MDSC by evaluating phagocytosis and cytotoxicity of MDSC against *E. coli* and *C. albicans*. The length the suppressive activity of MDSC can be maintained after stimulation with LF by culturing cells after washing LF with cytokines is tested for 1-3 days. Viability and functional activity is evaluated as described above.

Example 4: Evaluation of LF Effect on Suppressive Activity of Mouse MDSC In Vitro Currently, the typical way to generate mouse MDSC is to generate cells from BM HPC for 5-6 days in the presence of GM-CSF and IL-693

Functional activity of MDSC generated by using standard method and in the presence of different concentrations of LF will be compared. Viability and functional activity of isolated PMN (pull down of Ly6G+ cells with magnetic beads, Miltenyi) and MON (cell sorting of CD11b+Ly6G-Ly6Chi cells) will be tested with antigen non-specific (CD3/CD28 stimulation) and specific (OT-1 splenocytes in the presence of specific peptide) T-cell proliferation and IFN-γ production. Phagocytosis and cytotoxicity of MDSC against *E. coli* and *C. albicans* will be tested.

Evaluation of in vivo effects of LF induced MDSC. Ex vivo generated MDSC will be used for the treatment of BPD and NEC. The model of BPD is described in specific aim 1. At the initiation of hyperoxia, mice will be randomized to one of five groups. Group 1 will receive PBS, 2—PMN generated without LF, 3—LF induced PMN-MDSC, 4—MON generated without LF, and 5—LF induced M-MDSC. The number of cells will vary from 0.5 to $2\times10^6$ cells per mouse. Cells will be injected i.p. at the time of initiation of hyperoxia and 24 hrs later. Whether infused PMN- or M-MDSC are found in the lung either at 4 days of age (the end of hyperoxic exposure) or at 78 or 15-16 days of age will be determined. Since male and female mice respond differently in this model, we will perform experiments with 10 mice of each gender. NEC model has been described previously 49, 94. Neonates on days 3-4 of life will be taken from the parents and were fed with formula (Esbilac, PetAg, Hampshire, IL, USA) via oral gavage (100-200 μl, 3-4 times/day) during the observation time. Mice were gavaged with bacteria obtained from fecal suspension of adult healthy mice caecum at $7\times10^7$ CFU/mouse. Starting the next day, mice will be subjected to hypoxia-cold shock cycles twice a day for 3 days. Mice will be put in a hypoxia chamber at 1% O2 for 2 min and then immediately transferred to an ice slurry in a pre-cold bucket for 10 min. After shock, the mice are put back in the cage and observed for NEC symptoms, including severe abdominal distension, apnea, cyanosis, and lethargy. Small intestines are collected for histological examination. Fluorescein isothiocyanate (FITC) labeled dextran (FD7000, molecular weight 73,000) (Sigma-Aldrich Inc., St. Louis, MO) will be used to assess mucosal permeability as described previously 95. Different number (0.5 to $2\times106$) of MDSC generated as described in 3.2. will be injected i.p. 1 h before initiation of the NEC procedure, and repeated 48 hrs later. The severity of NEC will be assessed by inflammation score, mucosal permeability, and survival. Intestinal bacterial loading will be quantified with bacteria-specific 16s primers, as described previously 70.

The presence of Th17 and Treg in the lung and intestine after treatment with MDSC will be assessed in both models. Th17 will be detected by immunohistochemistry as CD4+ IL-17A+ and Rorγt+ cells, Treg as FoxP3+ cells. It is anticipated that LF induced MDSC have potent antibacterial activity and reduced lung and intestinal inflammation associated with inhibition of Th17 cells.

Example 5: Ex Vivo Differentiation of MDSCs

Whole peripheral blood is extracted from human subjects. Peripheral blood mononuclear cells are separated from whole blood, after which $10\times10^6$ PBMCs are cultured in 75% CM and 25% Iscove's Modified Dulbecco's medium (IMDM, Sigma-Aldrich) supplemented with 10% fetal clone I (FCI, GE Health Care Life Sciences, Hyclone Laboratories, Utah, USA), 100 U/ml penicillin, 100 μg/ml streptomycin (Sigma-Aldrich), 2 mM L-glutamine (Sigma-Aldrich) plus Lactoferrin for 6 days.

Cell viability and cell numbers are evaluated by trypan blue staining (Sigma-Aldrich). To evaluate the morphology of the cells, $5\times105$ sorted MDSC are fixed on glass slides using the cytospin technique and are centrifuged at a speed of 1000 rpm for 5 minutes.

Testing

Staining of cell surface markers is performed as described [67]. The following antibodies are used: anti-CD11b-eF450, anti-MHC II-PE, anti-F4/80-APC-H7 (eBioScience), anti-CD11b-FITC, anti-Ly6G-AF647, anti-Ly6C-Pe-Cy7, anti-CD80-BV421, anti-PD-L1-PE, anti-CD3-PercP-Cy5.5, anti-CD11c-AF647 (Biolegend, London, United Kingdom), anti-Ly6G-PE-CF594, anti-CD8-FITC (Becton Dickinson, Erembodegem, Belgium) and anti-CD45-VioBlue (130-102-775) (Mitenyi Biotec). For intracellular staining, cells are treated with inside FIX and incubated for 20 minutes at room temperature. Cells are incubated with PERM (Miltenyi Biotec) and the anti-arginase-1-PE (R&D systems, Abingdon, United Kingdom) or anti-iNOS-PercP-Cy5.5 (Santa Cruz Biotechnology, Heidelberg, Germany) antibody for 20 minutes at room temperature. Subsequently, cells are washed. Cells stained with isotype matched control antibodies served as a control. Cells are acquired using the LSR Fortessa (Becton Dickinson) and analysis was performed.

To evaluate the suppressive activity of MDSC, we performed an in vitro T-cell suppression assay. To that end, CD8+ T lymphocytes are isolated from the spleen of Balb/c mice using the CD8α+ T cell Isolation Kit II (Miltenyi Biotec). These CD8α+ T lymphocytes are labeled with carboxyfluorescein diacetate succinimidyl ester (CFSE, Life Technologies, Gent, Belgium). First, cells are washed and suspended in 5 ml phosphate buffered saline (PBS, Sigma-Aldrich) containing 0.1% bovine serum albumin (BSA, Life Technologies). Five ml of 0.5 μM CFSE are added to the cell suspension. The single cell suspension was incubated at 37° C., 5% CO2 for 10 minutes, washed in serum free Optimem (Invitrogen, Life Technologies), centrifuged for 7 minutes at 1500 rpm and suspended in 5 ml Optimem. Cells are plated at 1×105 cells in 100 μl in a 96-well. Subsequently, the cells are either left unstimulated or are stimulated with a 1/800 dilution of anti-CD3/anti-CD28 coated beads (Invitrogen). Enriched Ly6G+ or Ly6C+ MDSC are obtained using the Myeloid-Derived Suppressor Cell Isolation Kit (Miltenyi Biotec). Sorted MDSC are added to the stimulated T cells at the indicated MDSC to T cell ratios. When indicated, specific inhibitors for arg-1 (Nω-hydroxy-nor-Arginine (Nor-NOHA), 300 μM) (Enzo Life Sciences, Antwerpen, Belgium) or iNOS (aminoguanidine (AG), 1 mM) (Sigma-Aldrich) are added. Dilution of CFSE was evaluated 3 days later by flow cytometry as a measure of T-cell proliferation. To that end, T cells are additionally stained with anti-CD3-PercP-Cy5.5 (Biolegend). Data are collected using the FACSCanto Flow Cytometer (Becton Dickinson) and are analyzed with FlowJo 7.6 (Treestar Inc.). During the analysis, cells are gated according to their forward and side scatter distribution and to CD3 expression. Alternatively, supernatants are collected and screened for IFN-γ content using a standard ELISA (Thermo scientific) according to manufacturer's instructions.

Example 2: Generation of MDSC from Cord Blood CD34+ Cells

Isolated CD34+ cells were cultured and expanded in 25-T flasks (Corning, USA). After 6 days' culture, expanded cells were cultured in a supplement bottle turning device (HERAcell 240i, Thermo Fisher Scientific, USA). Culture bottles were placed horizontally in an incubator at 37° C. with 5% CO2 in the air with a rotation rate set at 0.82 U per minute (min). Cells were cultured in a modified medium based on Iscove's modified Dulbecco's medium (IMDM) (Life Technologies, USA) after the addition of nutrition supplements [24, 25] consisting of putrescine (100 μM), selenium (5 ng/mL), insulin (25 μg/mL), transferrin (50 μg/mL), and B-27 Supplements (2%, v/v). A staged culture protocol was designed for ex vivo expansion and differentiation, which included Stage 1 (days 0-6), Stage 2 (days 7~9), Stage 3 (days 10~15), and Stage 4 (days 16~18), respectively, fresh cytokines are replaced every three days. To optimize progenitor cell proliferation and neutrophil differentiation, different combinations of growth factors and cytokines, including SCF, Flt-3L, G-CSF, GM-CSF, IL-3, TPO, and fetal bovine serum (FBS) (10%, v/v, Hyclone, USA), were supplemented to modified culture media at various concentrations (Table 1). Culture optimization was carried out in a 2 L-bottle with 200 ml medium. Once the optimal culture condition was achieved and finalized, Take three independent cord blood samples as described above for CD34+ hematopoietic stem cell separation method, part of isolated CD34+ cells (5×105) were cultured and expanded in 25-T flasks. After 6 days' culture, expanded cells were cultured in the same-size bottle containing 600 ml medium. Cells were sub-cultured and cryopreserved to maintain an optimal cell density which ranged from 2×105 to 1×106 cells/ml [26].

In Vitro Bacterial Killing Assay

*Escherichia coli* BL21 was picked from single colonies grown on LB-agar plates, inoculated into LB broth and grown for 18 h at 37° C. Microorganisms were pelleted by centrifugation at 2000 g for 5 min, transferred into a microtube, washed once in 0.9% NaCl solution by centrifugation at 12,000 g for 10 s, and suspended in 1.5 ml 0.9% NaCl solution. Bacterial concentration was determined by measurement of turbidity at 500 nm. Suspensions were diluted to 1×108 cells/ml in 1 ml medium [28], HEPES-buffered saline with 10% human AB serum and opsonized for 30 min at 37° C. in a shaking water bath. Opsonized bacteria were kept on ice until use. Neutrophils were suspended in 100 μl HEPES-buffered saline with 40% human AB serum at a concentration of 5×106/ml. The opsonized *E coli* were added to the suspension of neutrophils at a neutrophil/bacterium ratio of 2:1. After incubation for 1 h, 50 μL of aliquots with and without neutrophils were diluted in 2.5 ml alkalinized water (pH 11) for neutrophils lysis. All the samples were then inverted twice. After standing for 5 min at room temperature and then vortex vigorously for 5 s, 50 μl of the samples were diluted in PBS to achieve a bacterial concentration of about 2×103/ml. Ten microliter aliquots of the diluted suspensions were spread on LB with 1.5% agar. Bacterial colonies were counted after overnight incubation.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

SEQUENCE LISTING FREE TEXT

Sequences 2-12-<223>-Constructed Sequence

What is claimed is:

1. A method of generating Myeloid-derived suppressor cells (MDSCs) ex vivo, the method comprising culturing blood cells with lactoferrin for about 1 hour to about 48 hours, wherein said blood are umbilical cord blood cells or blood cells from a newborn subject.

2. The method of claim 1, wherein the blood cells are selected from peripheral blood mononuclear cells, cord blood, and bone marrow cells.

3. The method claim 1, wherein the lactoferrin is present in an amount from 0.3-1.0 mg/ml.

4. The method claim 1, wherein the culture medium further comprises IL-6.

5. The method of claim 1, wherein said MDSCs have the phenotype of CD11b+CD14−CD15+, CD11b+CD14−CD66b+, or CD11b+CD14+HLA-DR-/loCD15−.

6. The method of claim 1, wherein said MDSCs have T cell suppressive activity.

7. The method of claim 1, further comprising removing said blood cells from a subject prior to culturing said cells.

8. The method of claim 1, further comprising isolating PBMCs from whole blood prior to, and culturing said PBMCs.

9. The method of claim 1, further comprising isolating or enriching CD14+cells or PMN.

10. The method of claim 1, further comprising culturing CD34+progenitors to generate PMN and/or monocytes.

11. A pharmaceutical composition comprising the MSDCs of claim 1 and a pharmaceutical carrier.

12. A method of treating an inflammatory disease in a subject comprising administering the pharmaceutical composition of claim 11.

13. The method according to claim 12, wherein the subject is a child.

14. The method according to claim 13, wherein the child is a newborn.

15. The method according to claim 12, wherein the composition comprises $1 \times 10^5$ to $1 \times 10^{14}$ cells.

16. The method according to claim 12, wherein the method comprises removing blood cells from the subject prior to culturing said cells with LF.

17. A method of preventing, reducing the likelihood of occurrence or severity of an inflammatory disease in a subject, the method comprising administering the pharmaceutical composition of claim 11.

* * * * *